United States Patent
Parhami et al.

(10) Patent No.: US 10,421,773 B2
(45) Date of Patent: Sep. 24, 2019

(54) BONE-SELECTIVE OSTEOGENIC OXYSTEROL BISPHOSPHONATE ANALOGS

(71) Applicant: The Regents of the University of California, Oakland, CA (US)

(72) Inventors: Farhad Parhami, Los Angeles, CA (US); Frank Stappenbeck, Los Angeles, CA (US); Brian T. Chamberlain, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/302,154

(22) PCT Filed: May 1, 2015

(86) PCT No.: PCT/US2015/028917
§ 371 (c)(1),
(2) Date: Oct. 5, 2016

(87) PCT Pub. No.: WO2015/168636
PCT Pub. Date: Nov. 5, 2015

(65) Prior Publication Data
US 2017/0022244 A1 Jan. 26, 2017

Related U.S. Application Data

(60) Provisional application No. 61/987,739, filed on May 2, 2014.

(51) Int. Cl.
| | | |
|---|---|---|
| C07J 41/00 | (2006.01) |
| C07J 9/00 | (2006.01) |
| C07J 51/00 | (2006.01) |
| A61K 35/32 | (2015.01) |
| C07J 7/00 | (2006.01) |
| C07J 43/00 | (2006.01) |

(52) U.S. Cl.
CPC ........... *C07J 41/0055* (2013.01); *A61K 35/32* (2013.01); *C07J 9/00* (2013.01); *C07J 51/00* (2013.01); *C07J 7/002* (2013.01); *C07J 43/003* (2013.01)

(58) Field of Classification Search
CPC ........... C07J 9/00; C07J 41/0055; C07J 51/00
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,992,478 A | 2/1991 | Geria |
| 5,183,815 A * | 2/1993 | Saari .................. C07F 9/405 514/172 |
| 8,071,575 B2 * | 12/2011 | Pierce, Jr. .............. A61K 31/70 514/169 |
| 2011/0008297 A1 | 1/2011 | Parhami et al. |

FOREIGN PATENT DOCUMENTS

| | | |
|---|---|---|
| EP | 0 496 520 A1 | 7/1992 |
| EP | 0 555 845 A2 | 8/1993 |
| EP | 0 555 845 A3 | 8/1993 |
| JP | H-04352795 A | 12/1992 |
| JP | 2007-518746 A | 7/2007 |
| WO | WO-2005/070952 A1 | 8/2005 |
| WO | WO-2007/098281 A2 | 8/2007 |
| WO | WO-2007/098281 A3 | 8/2007 |
| WO | WO 2012/024584 A2 * | 2/2012 ............. A61K 31/58 |
| WO | WO-2013/169397 A1 | 11/2013 |
| WO | WO-2013/169399 A1 | 11/2013 |

OTHER PUBLICATIONS

Bortolini, O. et al. (Jun. 2012, e-published Mar. 19, 2012). "Synthesis, characterization and biological activity of hydroxyl-bisphosphonic analogs of bile acids," *Eur J Med Chem* 52:221-229.
Cosman, F. (Dec. 2014). "Anabolic and antiresorptive therapy for osteoporosis: combination and sequential approaches," *Curr Osteoporos Rep* 12(4):385-395.
Gil, L. et al. (May 1999). "Prostaglandin E2-bisphosphonate conjugates: potential agents for treatment of osteoporosis," *Biorg Med Chem* (795):901-919.
Gill, S. et al. (Nov. 2008, e-published May 6, 2008). "Sterol regulators of cholesterol homeostasis and beyond: the oxysterol hypothesis revisited and revised," *Prog Lipid Res* 47(6):391-404.
Johnson, J.S. et al. (Jun. 2011). "Novel oxysterols have pro-osteogenic and anti-adipogenic effects in vitro and induce spinal fusion in vivo," *J Cell Biochem* 112(6):1673-1684.
Kha, H.T. et al. (May 2004, e-published Jan. 12, 2004). "Oxysterols regulate differentiation of mesenchymal stem cells: pro-bone and anti-fat," *J Bone Miner Res* 19(5):830-840.
Khosla, S. et al. (Jul. 2012, e-published Apr. 20, 2012). "Benefits and risks of bisphosphonate therapy for osteoporosis," *J Clin Endocrinol Metab* 97(7):2272-2282.
Montgomery, S.R .et al. (Aug. 2014). "A novel osteogenic oxysterol compound for therapeutic development to promote bone growth: activation of hedgehog signaling and osteogenesis through smoothened binding," *J Bone Miner Res* 29(8):1872-1885.
Muschitz, C. et al. (Jan. 2013). "Antiresorptives overlapping ongoing teriparatide treatment result in additional increases in bone mineral density," *J Bone Miner Res* 28(1):196-205.
Page, P.C. et al. (Jun. 1, 2001). "Novel synthesis of bis(phosphonic acid)-steroid conjugates," *J Org Chem* 66(11):3704-3708.
Petrova, N.S. et al. (Mar. 2012, e-published Nov. 10, 2011). "Carrier-free cellular uptake and the gene-silencing activity of the lipophilic siRNAs is strongly affected by the length of the linker between siRNA and lipophilic group," *Nucleic Acids Res* 40(5):2330-2344.
Richardson, J.A. et al. (Apr. 1, 2007). "Oxysterol-induced osteoblastic differentiation of pluripotent mesenchymal cells is mediated through a PKC- and PKA-dependent pathway," *J Cell Biochem* 100(5):1131-1145.

(Continued)

*Primary Examiner* — Pancham Bakshi
(74) *Attorney, Agent, or Firm* — Mintz; Irina Britva; Kenneth Jenkins

(57) ABSTRACT

Oxysterol-bisphosphonate and oxysterol-alendronic acid compounds, compositions including them, and methods using them for the treatment of bone disorders.

18 Claims, 5 Drawing Sheets

(56) References Cited

OTHER PUBLICATIONS

Schroepfer, G.J. Jr. (Jan. 2000). "Oxysterols: modulators of cholesterol metabolism and other processes," *Physiol Rev* 80(10):361-554.

Silva, B.C. et al. (2011). "New approaches to the treatment of osteoporosis," *Annu Rev Med* 62:307-322.

Sottero, B. et al. (2009). "Cholesterol oxidation products and disease: an emerging topic of interest in medicinal chemistry," *Curr. Med. Chem.* 16(6):685-705.

Vachal, P. et al. (Jun. 1, 2006). "Synthesis and study of alendronate derivatives as potential prodrugs of alendronate sodium for the treatment of low bone density and osteoporosis," *J Med Chem* 49(11):3060-3063.

Vescini, F. et al. (Jan. 2012, May 29, 2012). "PTH 1-84: bone rebuilding as a target for the therapy of severe osteoporosis," *Clin Cases Miner Bone Metab* 9(1):31-36.

Extended European Search Report dated Nov. 2, 2017, for EP Patent Application No. 15786795.3, 8 pages.

International Search Report dated Jul. 27, 2015, for PCT Application No. PCT/US2015/028917, filed May 1, 2015, 5 pages.

Written Opinion dated Jul. 27, 2015, for PCT Application No. PCT/US2015/028917, filed May 1, 2015, 7 pages.

\* cited by examiner

BONE-SELECTIVE OSTEOGENIC OXYSTEROL BISPHOSPHONATE ANALOGS

This application is a U.S. National Stage Entry of PCT/US2015/028917, filed May 1, 2015; which claims the benefit of priority from U.S. Provisional Patent Application No. 61/987,739, filed May 2, 2014, all of which are hereby incorporated by reference in their entirety.

This invention was made with Government support under AR065808 awarded by the National Institute of Arthritis and Musculoskeletal and Skin Diseases. The Government has certain rights in the invention.

BACKGROUND

Osteoporosis is the most common metabolic bone disease affecting more than 10 million Americans, nearly 50% of the elderly female and more than 10% of the elderly male population. (Rachner, T. D.; et al. *Lancet* 2011, 377, 1276-1287. Silva, B. C. *Annu. Rev. Med.* 2011 62, 307-322. Lyritis, G. P; et al. *Ann. N. Y. Acad. Sci.* 2010, 1205, 277-283. Khosla, S.; et al. *J. Clin. Endocrinol, Metab.* 2012, 97, 2272-2282. Aspray, T. J.; et al. *Maturitas* 2012, 71, 76-78. Black, D. M.; et al. *N. Engl. J. Med.* 2012, 366, 2051-2053.) Osteopenia (reduced bone mass), a major risk factor for developing osteoporosis, is even more common, affecting 34 million Americans. Bone fractures are a widespread complication of osteoporosis and osteopenia resulting in significant socio-economic cost, such as hospitalization and disability, and very often they are the cause of deterioration and death of otherwise healthy and functioning elderly individuals. Age-related osteoporotic bone loss and its resulting complications cause significant morbidity and mortality in the aging population.

Bone health in adult life depends on a coordinated balance of anabolic and catabolic cellular activities of bone-forming osteoblasts and bone-resorbing osteoclasts, respectively. Multipotent mesenchymal stem cells (aka marrow stromal cells, MSCs) form the precursor population for a variety of cell types, including osteoblasts and adipocytes. Formation of new bone is driven by osteoblastic differentiation of MSCs, a process that can be disrupted by a number of factors. Aging, disease and lifestyle factors such as tobacco and alcohol abuse tend to push MSC populations toward adipogenesis at the expense of osteoblast differentiation, resulting in osteopenic disorders that often lead to full-fledged osteoporosis and impaired fracture repair. The mechanisms behind lineage-specific differentiation of MSC can be important. Factors can stimulate osteoblast formation while inhibiting adipogenesis.

Among two possible therapeutic strategies for osteoporosis, prevention of bone loss/resorption or stimulation of bone growth, anti-resorptive therapy with bisphosphonate drugs is more established. (Khosla, S.; et al. *J. Clin. Endocrinol. Metab.* 2012, 97, 2272-2282 Sharpe, M.; Noble, S.; Spencer, C. M. Drugs. 2001, 61, 999-1039.) Nearly all current therapies for osteoporosis as well as the majority of potential new treatments under clinical investigation aim to reduce the level of bone resorption in osteoporotic patients. Therapies on the market or in clinical trials that target mechanisms of bone resorption include Denosumab (Prolia), Zolendronic Acid (Reclast), Odanacatib, and Saracatinib. Anti-resorptive drug therapy has been most effective in treating early and mild cases of the disease, unlike advanced osteoporosis where a massive loss of bone mineral density has already occurred.

Alternatively, bone anabolic agents can provide additional treatment options, particularly with advanced disease, and significantly improve osteoporosis management, in spite of a paucity of FDA approved drugs in this area. Currently, the only FDA approved bone anabolic agent available for treatment of severely osteoporotic patients is teriparatide (Forteo), a recombinant form of parathyroid hormone (PTH), which has to be administered intermittently, by daily injection. Forteo can produce significant bone formation and reduce fracture risk, but its use is severely restricted due to safety concerns. Due to adverse side effects, such as an increased risk of osteosarcoma, drug labeling for Forteo is highly restricted with respect to patient population and duration of use (less than 24 months). (Cosman, F.; et al. *Curr. Osteoporos. Rep.* 2014, 12, 385-395. Muschitz, C.; et al. *J. Bone Miner. Res.* 2013, 28, 196-205. Vescini, F.; et al. *Clin. Cases Miner. Bone Metab.* 2012, 9, 31-36.) Other anabolic agents under clinical investigation include calcilytic drugs that stimulate endogenous intermittent PTH secretion, antibodies to an inhibitor of osteoblasts called Sclerostin, and inhibitors of antagonists of Wnt signaling. (Silva, B. C.; et al. *Annu. Rev. Med.* 2011 62, 307-322)

In patients with mild osteoporosis, bisphosphonate drugs (e.g., alendronic acid, Fosamax) can produce significant benefits such as improved bone density and reduced fracture risk. However, bisphosphonate drugs, including alendronic acid, display low oral bioavailability, 0.6-0.7% on average, even when ingested under fasting conditions. Drug intake together with meals and beverages (other than water) further reduces the bioavailability, and intake under fasting conditions entails serious upper GI tract irritation in a majority of patients. Hence, repeated, often daily, oral dosing under fasting conditions is necessary to maximize delivery of the bisphosphonate drugs to what is pharmacologically achievable while more than 99% of the dose cannot be absorbed and is ejected from the body unused. The fraction of bisphosphonate drug that can be absorbed, can rapidly partition in the human body, with about 50% of the drug binding to bone surface and the rest being excreted unchanged via the kidneys. The physicochemical basis of low oral absorption is thought to be associated with the negatively charged phosphonate moieties that are unavoidably part of all bisphosphonate drugs. To overcome this drawback, strategies have been investigated, including prodrug approaches with fatty acid and bile acid conjugation that aim to mask the phosphonate charge effect. (Bortolini, O.; et al. *Euro. J. Med. Chem.* 2012, 52, 221-229. Vachal, P.; et al. *J. Med. Chem,* 2006, 49, 3060-3063.)

Naturally-occurring oxysterols can act as drug-like molecules with an effect on MSCs and other multipotent mesenchymal cells. Oxysterols that occur in human circulation and various tissues can be short-lived intermediates in metabolic transformations of cholesterol to form steroid hormones and bile acids. Beyond their role as passive metabolites, however, natural oxysterols can function as signaling molecules, capable of modulating a range of physiological phenomena, among them homeostasis of lipids as well as control over cellular states such as differentiation, inflammation and apoptosis. That is, oxysterols can play a role as regulators of tissue specific signaling. Early research on oxysterols considered their pathological contributions and assumed that all oxysterols have similar properties, regardless of their distinct chemical composition. Oxysterol chemotypes can have more individualized characteristics that depend on the cellular context and the exact chemical composition of the oxysterol. (Schroepfer, G. J. *Physiol. Rev.* 2000, 80, 362-554. Gill, S.; et al. *Prog. Lipid*

Res. 2008, 47, 391-404. Sottero, B.; et al. *Curr. Top. Med. Chem.* 2009, 16, 685-705.) Some oxysterols can promote oxidative stress. However, osteogenic oxysterols can inhibit the adverse effects of oxidative stress on osteogenic differentiation of progenitor cells. Some oxysterols are thought to be endogenous ligands of Liver X Receptors (LXR). However, the osteogenic activity of oxysterols may not be a consequence of LXR activation, but can be mediated through the activation of Hh signaling. The oxysterol-induced activation of Hh signaling can occur independent of Hh proteins and result in the activation of non-canonical Wnt and Notch signaling. Baseline PKA/cAMP, PKC, MAPK, and PI3-Kinase signaling can be involved in mediating various aspects of the cellular responses to these oxysterols. (Kha, H. T.; et al. *J. Bone Miner. Res.* 2004, 19, 830-840. Richardson, J. A.; et al. *J. Cell. Biochem.* 2007, 100, 1131-1145.) In spite of reported cytotoxicity of some oxysterols, no toxic effects were found with osteogenic oxysterols in vitro when dosed at 1-20 μM with osteoprogenitor cells or, in vivo, during local administration in the rat spine fusion model (40 mg), or, in mice, dosed ip at 50 mg/kg 3 times per week for a total of 8 weeks as determined by the absence of behavioral changes.

SUMMARY OF THE INVENTION

An embodiment of the present invention is a composition comprising an oxysterol-bisphosphonate compound, such as set forth herein, for example, an Oxy133-aldenronic acid compound. The composition can include a pharmaceutically acceptable carrier or diluent and can be a pharmaceutical formulation. A method of the present invention includes the delivery, locally and/or systemically, of the formulation into a subject, which can be a person or an animal, for the treatment of a bone disorder including, but not limited to, a bone fracture, osteoporosis, and/or osteopenia. A method of the present invention includes in vitro treatment of osteoblast progenitor cells with an oxysterol-bisphosphonate compound, and their (the osteoblast progenitor cells) subsequent localization and/or systemic delivery into a subject, which can be a person or an animal, for the treatment of a bone disorder including, but not limited to, a bone fracture, osteoporosis, and/or osteopenia. A method of the present invention includes making and/or administering, such as locally and/or systemically, a formulation including an oxysterol-bisphosphonate compound to a subject, to stimulate the Hedgehog signaling pathway in a tissue and/or organ, for example, a tissue and/or organ that would benefit from therapeutic activation of the Hedgehog signaling pathway.

An embodiment includes a compound having the formula with $R_1$, $R_2$, and $R_3$ independently selected from the group consisting of hydrogen,

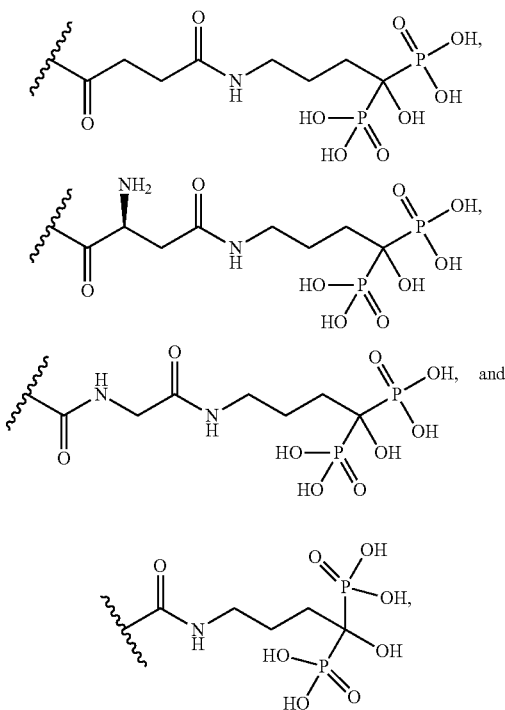

At least one of $R_1$, $R_2$, and $R_3$ can be other than hydrogen. $R^4$ can be alkyl of from 1 to 5 carbons. The compound can have the formula

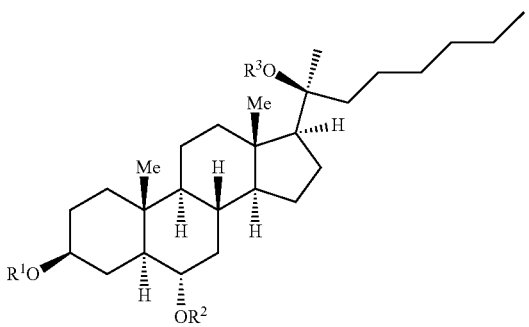

The compound can have the formula

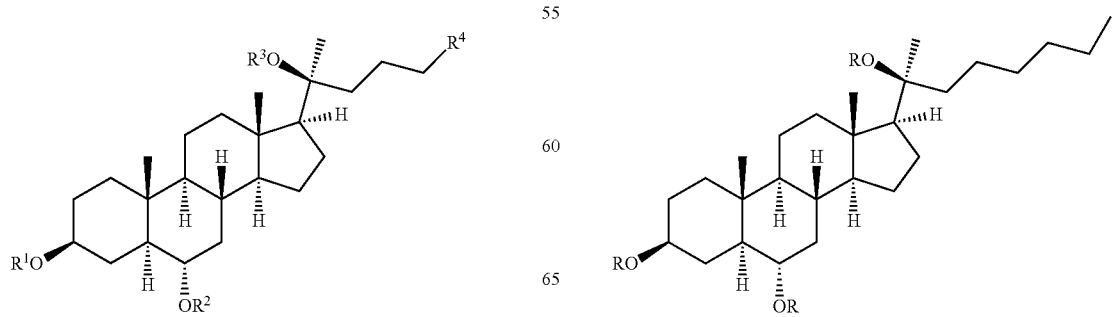

with R selected from the group consisting of

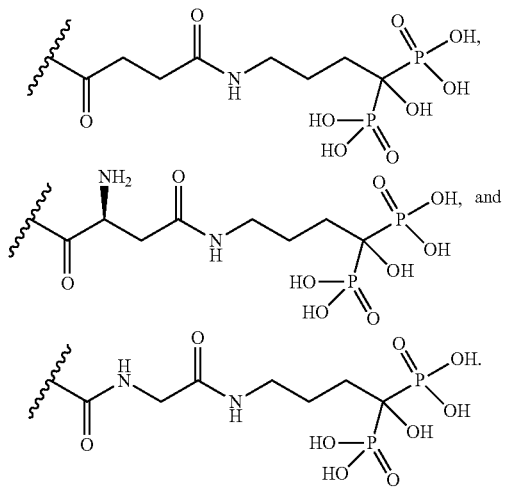

The compound can have the formula

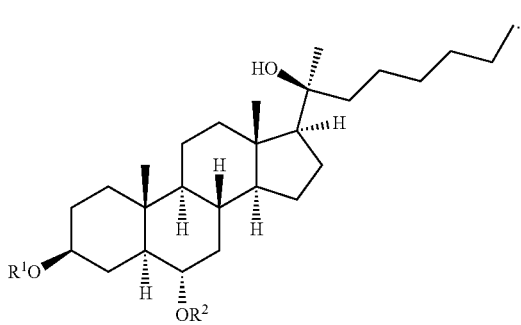

The compound can have the formula

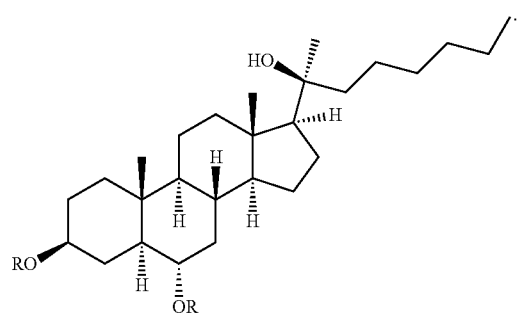

The compound can have the formula

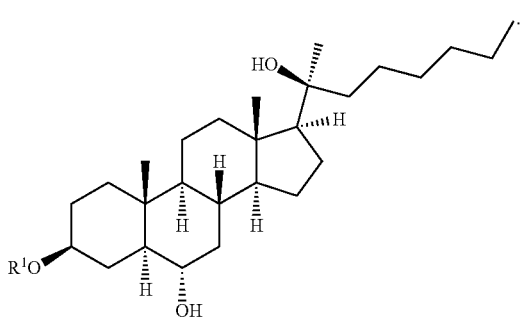

The compound can have the formula

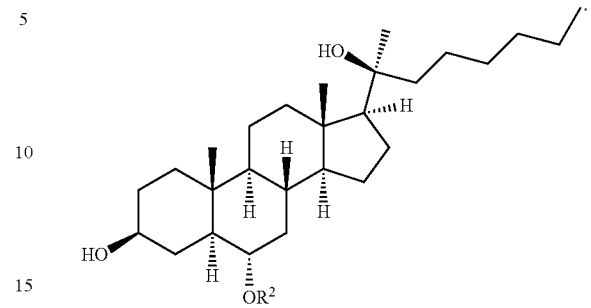

The compound can have the formula

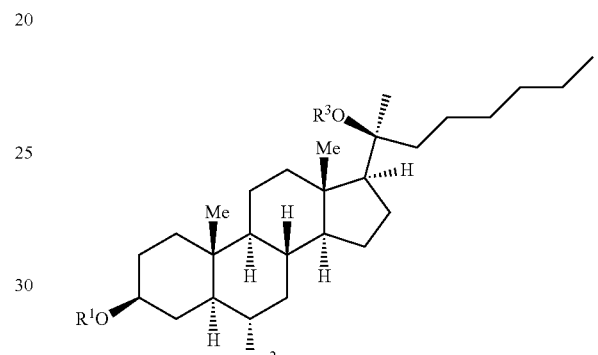

with $R_1$, $R_2$, and $R_3$ are independently selected from the group consisting of hydrogen,

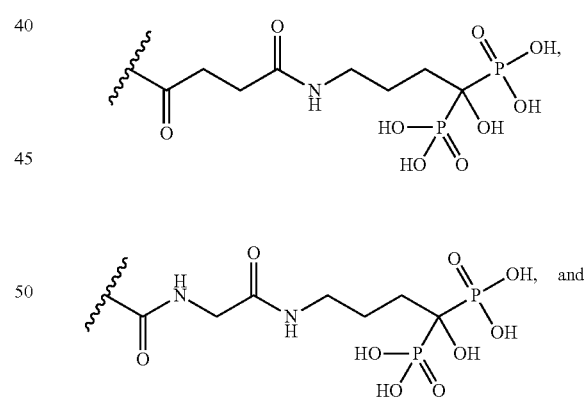

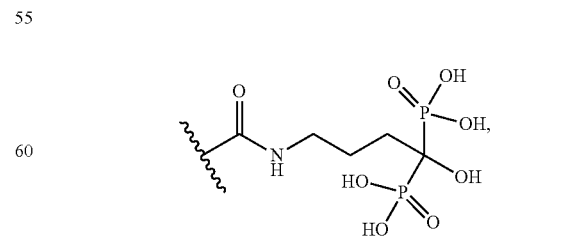

and pharmaceutically acceptable salts thereof. The compound can have the formula

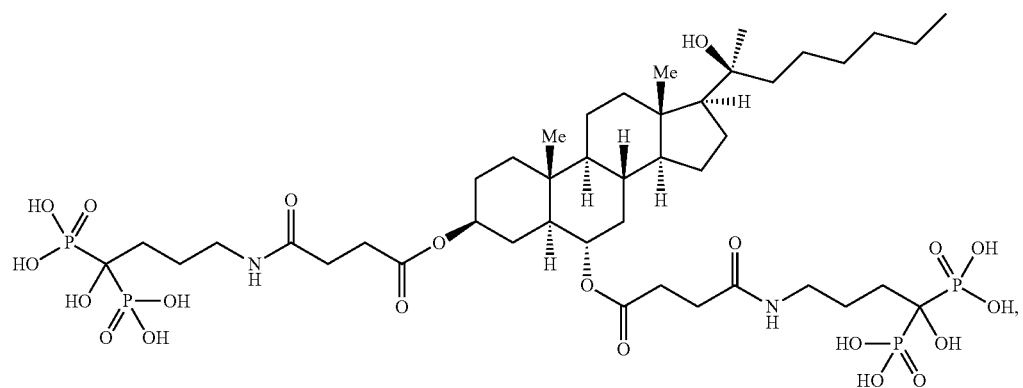
[Oxy166]
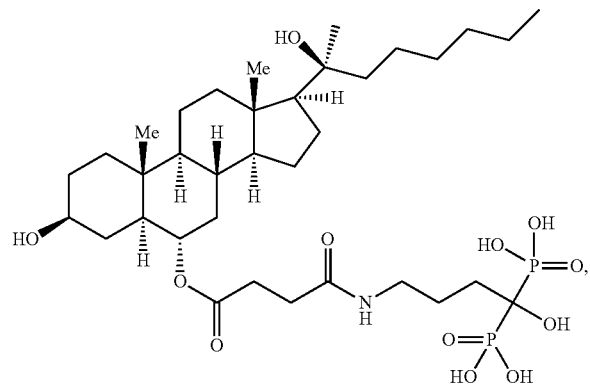
[Oxy167]
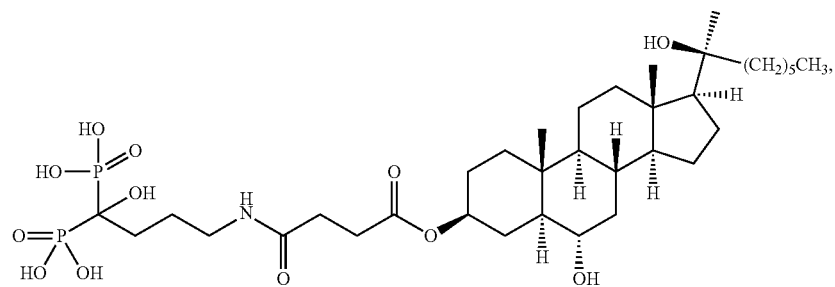
[Oxy174]
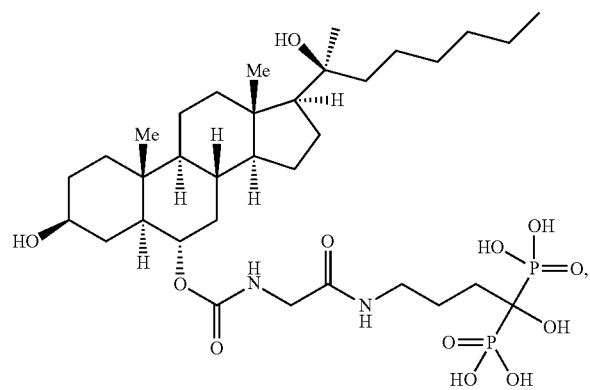
[Oxy175]

-continued
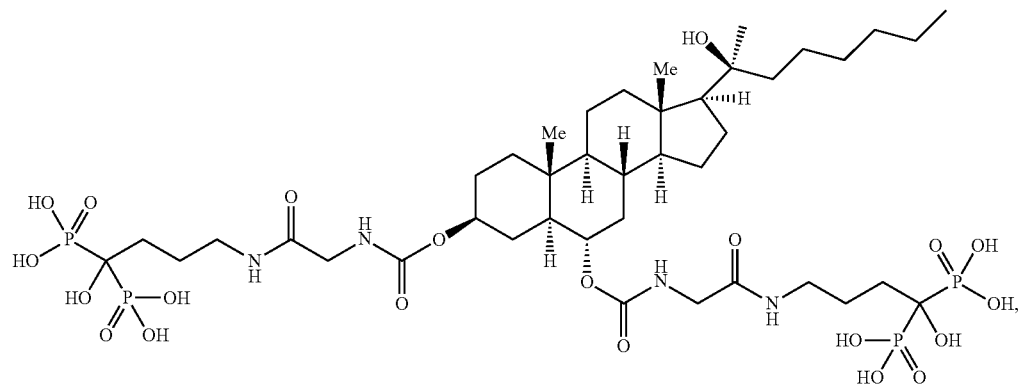
[Oxy176]
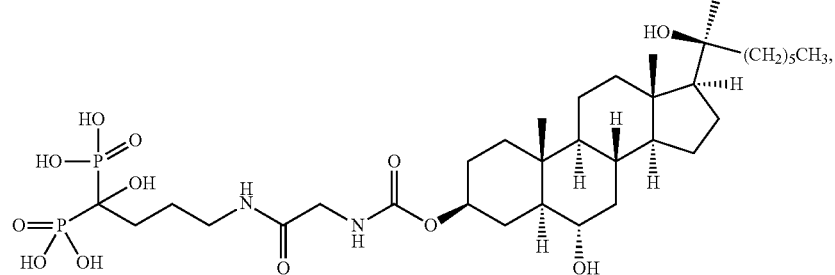
[Oxy177]
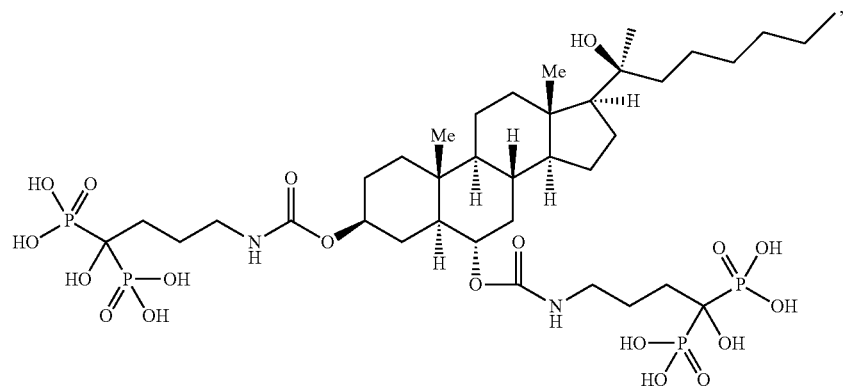
[Oxy178]
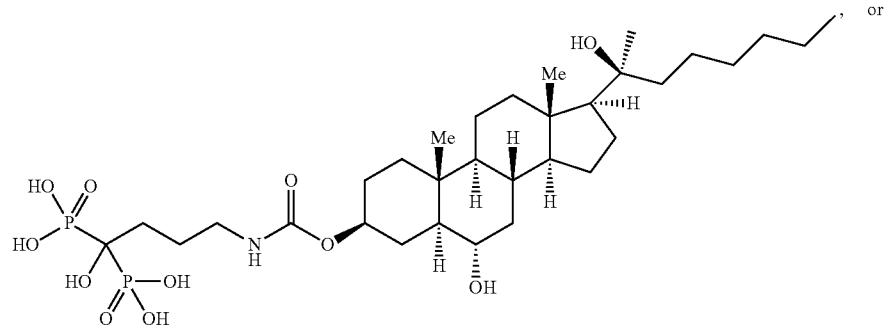
[Oxy178b]

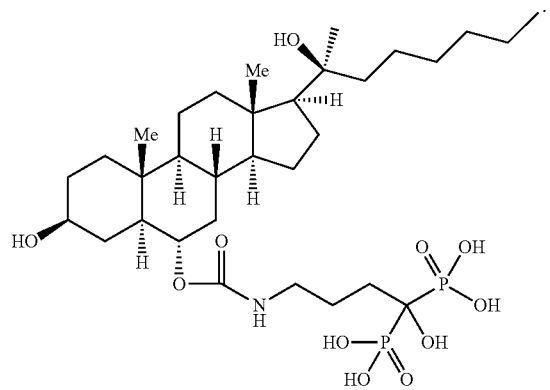

[Oxy178c]

An embodiment includes pharmaceutically acceptable salts of these compounds, and sodium salts of these compounds. An embodiment includes a pharmaceutical composition comprising one or more of these compounds and a pharmaceutically acceptable carrier or diluent.

A method according to the invention includes treating a human or an animal subject suffering from a bone disorder, by administering to the subject an effective amount of at least one of these compounds. The compound can be administered to effect localized or systemic delivery to the subject. For example, the bone disorder can be bone fracture, osteoporosis, or osteopenia. An osteoblast progenitor cell can be contacted with an effective amount of at least one of these compound, for example, in vitro. The contacted osteoblast progenitor cell can be administered to a subject, for example, locally or systemically.

A method according to the invention for treating a cell includes administering an effective amount of at least one of these compounds to the cell, so that a Hedgehog signaling pathway in the cell is stimulated. The cell can be part of a tissue or organ. The compound can be administered in vivo. A method according to the invention for treating a human or an animal subject that would benefit from therapeutic activation of a Hedgehog signaling pathway in a tissue or organ, includes treating a cell of a tissue or organ, so that the Hedgehog signaling pathway of the tissue or organ is stimulated.

An embodiment according to the invention includes one or more of these compounds for treating a bone disorder. An embodiment according to the invention includes the use of one or more of these compounds in the manufacture of a medicament for the treatment of a bone disorder.

DETAILED DESCRIPTION

Figure 1:
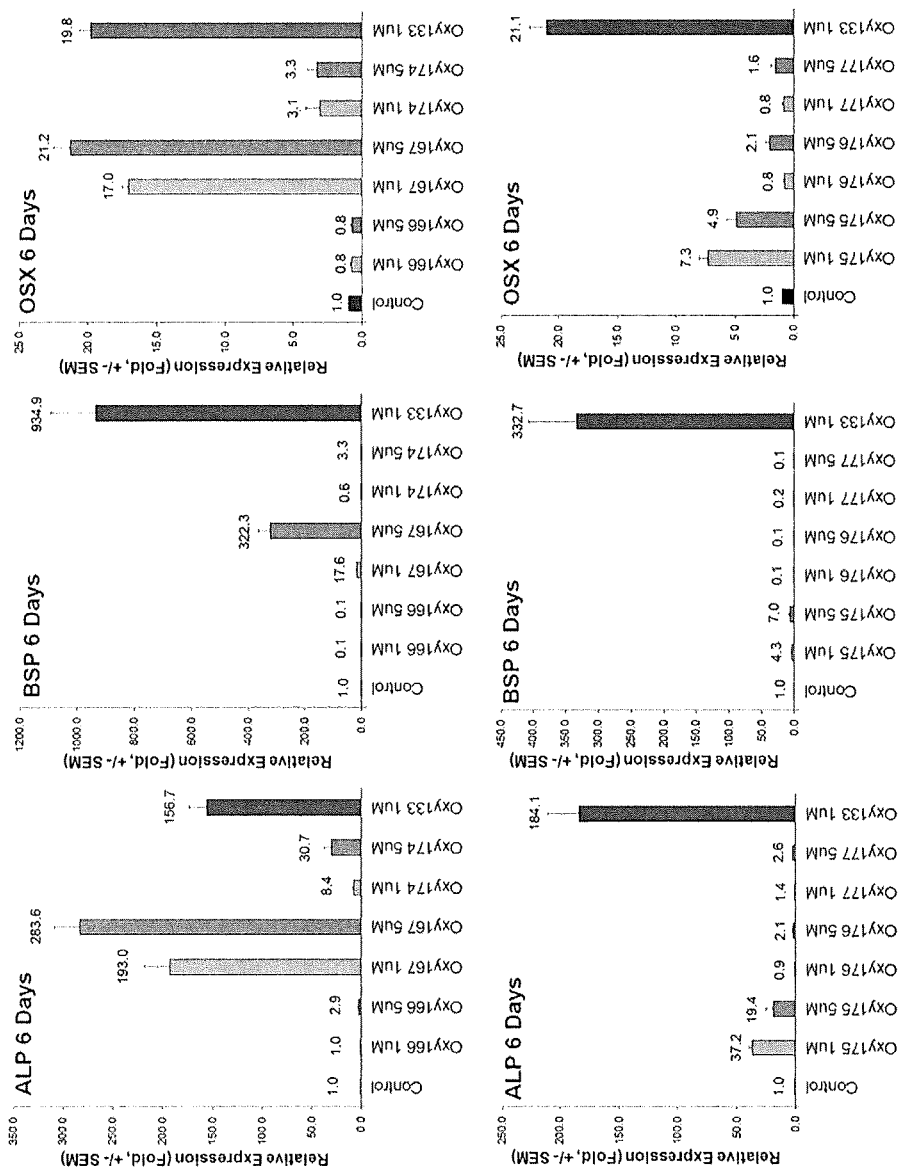
FIG. 1 shows the effect of OXY133-ALN conjugates in M2 cells on osteogenic gene expression for alkaline phosphatase (ALP), bone sialoprotein (BSP), and osterix (OSX) after 6 days (numbers above each bar represent the fold induction over the control).

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention.

Naturally-occurring oxysterols, 20(S)-hydroxycholesterol, 22(S)-hydroxycholesterol and 22(R)-hydroxycholesterol can be used as potential osteogenic agents. A series of potent osteogenic oxysterol analogues was identified, which are efficacious both in vitro and in vivo. Members of this family of semi-synthetic oxysterols induce robust bone formation and spine fusion in rats when applied locally between transverse processes via a collagen sponge. (Johnson, J. S.; et al. J. Cell. Biochem, 2011, 112, 1673-1684.)

Oxysterols, products of cholesterol oxidation, are formed in vivo, and have been implicated in various biologic processes including cellular differentiation and cholesterol metabolism. Naturally occurring oxysterols, which are found in human and animal circulation and in various tissues, can have bone-forming, osteogenic properties. The administration of these oxysterols to pluripotent mesenchymal osteoprogenitor cells, including bone marrow stromal cells (mesenchymal stem cells, MSC) and embryonic fibroblasts, can cause robust osteogenic differentiation and formation of an abundant mineralized bone matrix in vitro. Without being bound by theory, these effects may be mediated in part through activation of the Hedgehog (Hh) signaling pathway independent of the classical Hh proteins. A family of more potent oxysterols can possess osteogenic and anti-adipogenic activity superior to the naturally occurring oxysterols from which they are derived. Such molecules can display potent osteogenic activity in vitro and stimulate robust bone formation and spine fusion in vivo. They are not expected to elicit significant immunogenic responses.

OXY133 is an analog in the series with enhanced osteogenic activity. OXY133 can induce osteogenesis in cultured human primary mesenchymal stem cells and induce spine fusion in rats in an accelerated manner compared to other analogues. OXY133 can induce robust osteogenesis in non-rodent models of bone disease such as rabbit spine fusion and rabbit calvarial defect models. OXY133 is a drug development candidate for local administration with potential application in spine fusion and repair of non-union fractures. (Montgomery, S. R.; et al. *J. Bone Miner. Res.* 2014, 29, 1872-1885.) However, when contemplating systemic administration of oxysterols like OXY133 as a potential anabolic factor to stimulate bone formation in osteoporosis, one has to consider their short half-lives (<5 min) in human liver microsomes (HLM), and tissue distribution that does not necessarily favor deposition in bone tissue. Furthermore, due to the possible mechanism of osteogenesis, a transient activation of the Hh-pathway in MSCs, increasing selectivity for bone tissue while minimizing the exposure to other tissues may be prudent. This can be accomplished by linking the bisphosphonate alendronic acid to the oxysterol molecule that selectively delivers it to bone.

Bisphosphonates can inhibit bone resorption, and have bone selective affinity. Bisphosphonates when conjugated to other drugs can serve as bone specific drug delivery agents as they leave tissues other than bone largely unexposed.

The cellular differentiation of multipotent mesenchymal stem cells (MSCs) into bone forming osteoblasts can constitute a driver of anabolic bone growth. Certain naturally occurring oxysterols can induce osteogenic while preventing adipogenic differentiation of MSCs in vitro, and can stimulate localized bone formation in a rat calvarial defect model in vivo. The synthesis and characterization of novel semi-synthetic oxysterols with greater osteogenic activity than the naturally occurring oxysterols when used in vitro or in a rat spine fusion model in vivo has been reported. In an embodiment of the present invention, novel osteogenic oxysterols as bone anabolic agents in the context of systemic dosing (iv (intravenous), ip (intraparenteral), subcu (subcutaneous), or oral), as required for the treatment of osteoporosis, are set forth.

When administered systemically these molecules may selectively home to bone tissue and enhance bone formation. These molecules can be used as bone anabolic agents for the treatment of osteoporosis. Bone targeted osteogenic oxysterols are not expected to have any significant toxic or immunogenic effects when administered systemically.

An embodiment of the present invention includes osteogenic oxysterols formed by conjugating the oxysterol compound OXY133 to alendronic acid, a bisphosphonate drug. The OXY133-alendronic acid conjugated analogues can be used as systemically active bone anabolic agents for treatment of osteoporosis. The OXY133-alendronic acid conjugates can have increased selectivity for binding to hydroxyapatite and their efficacy in stimulating osteogenic differentiation of osteoprogenitor cells. The OXY133-alendronic acid conjugates can be used for intervention in osteoporosis that targets osteogenic differentiation of osteoprogenitor cells in vivo, stimulating new bone formation at various skeletal sites. Bisphosphonates display low oral availability and tolerability. Oxysterol-alendronic acid conjugates can have improved pharmacological properties. In order to minimize potential side effects and enhance delivery to the bone tissue, a potent osteogenic oxysterol is conjugated to alendronic acid.

In an embodiment of the invention, novel OXY133-ALN conjugate molecules are synthesized that are combinations of an osteogenic oxysterol, Oxy133, with a bisphosphonate molecule, alendronic acid. As shown below, a bisphosphonate-linker may be attached at the 3, 6, and/or 20 positions of OXY133:

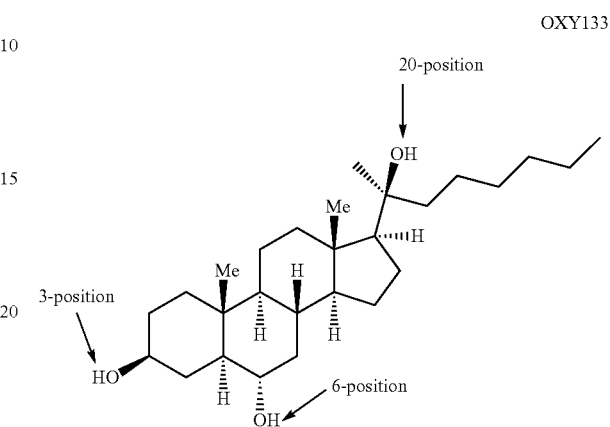

OXY133

Bone specific drug delivery is not only applicable to drugs marginally acceptable for bone disease (e.g., estradiol and diclofenac) to increase efficacy, minimize side effects and allow for appropriate dosing. In an embodiment of the present invention, the concept of bone specific drug delivery is applied to osteogenic molecules not previously tested for systemic bone disease, to render them as effective treatments for osteoporosis. Oxysterol-based agonists of Hh signaling with osteogenic properties can fall into this category. Bone specific drug delivery agents can be attached to their drug molecules via hydrolysable linker bonds. Non-hydrolysable bonds can be used in cases where the drug molecule after conjugation to the bone targeting unit retains pharmacological activity. Ester groups can be used, as they populate a favorable stability range relative to more labile thioesters and more stable amides. (Gil, L.; et al. *Bioorg. Med. Chem.* 1999, 7, 901-919.) The in vivo stability of ester groups can be further fine-tuned by substitutions placed adjacent to the ester group. Hence, Oxy133-alendronate ester conjugates can be used for systemic dosing (oral, ip, subcu, or iv) that entails selective deposition in bone tissue followed by enzymatic linker hydrolysis and release of the osteogenic agent, OXY133, at controlled rates into the target tissue.

In an embodiment of the invention, OXY133-ALN conjugates comprises one or more ALN conjugated to OXY133 through a linker at one or more position of OXY133. In an embodiment of the invention, ALN may be conjugated with OXY133 through a linker at positions 3, 6, and/or 20 of OXY133.

For example, as shown below, analogs 2, 3, and 4, in which OXY133 is conjugated to alendronic acid via the 3- and/or 6-positions with ester or carbamate linker units derived from succinic acid (a series), aspartic acid (b series), a glycine carbamate linker (c series), or a directly linked carbamate (d series). The carbamate linker can be more stable toward esterase hydrolysis compared to ester linkers, and the succinic acid-based linker can be more stable toward esterase hydrolysis compared to the aspartic acid-based linker, which may undergo enzymatic hydrolysis of the amino ester bond more readily. A difference in the rate of ester hydrolysis can beneficially be utilized to fine tune the release of OXY133 in the target bone tissue. The fully protonated forms of the conjugates are shown here for convenience, but any salt form of the bisphosphonic acid can be prepared. Typically the sodium salt of the conjugate is prepared.

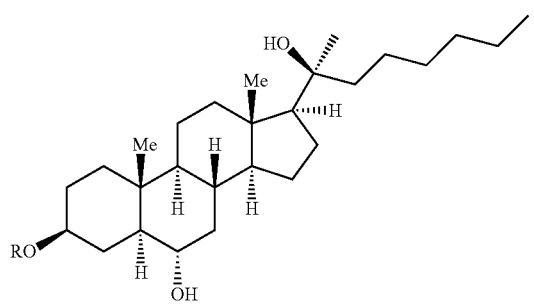

2 a, b, c, d

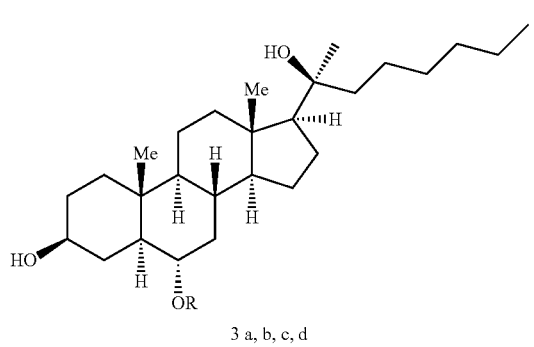

3 a, b, c, d

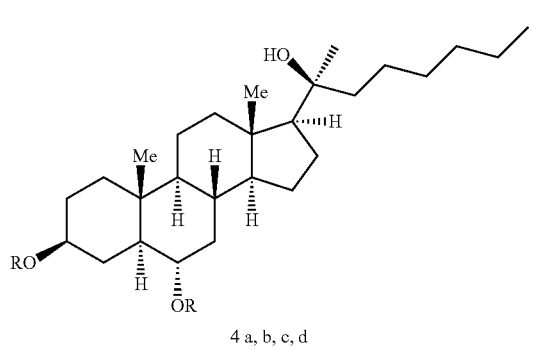

4 a, b, c, d

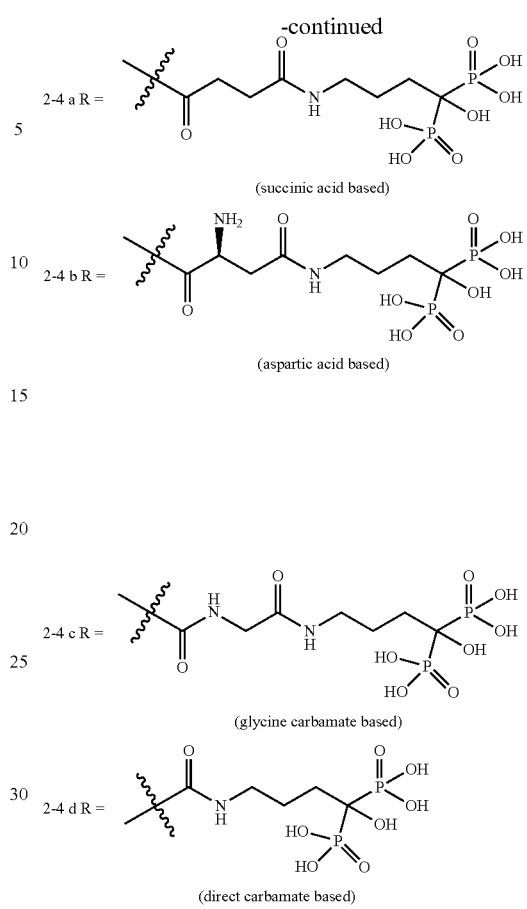

2-4 a R = (succinic acid based)

2-4 b R = (aspartic acid based)

2-4 c R = (glycine carbamate based)

2-4 d R = (direct carbamate based)

The final OXY133-ALN conjugates may be obtained through different synthetic routes. For example, the synthesis of the Oxy133-alendronate conjugates 2, 3, and 4 may start from pregnenolone 5, which can be transformed to differentially protected OXY133 derivatives, 6, by protection of the 3-hydroxyl, addition of the side chain, hydroboration-oxidation of the 5-alkene, and then, depending on the analog desired, selective protection or deprotection of the hydroxyl groups, as shown below:

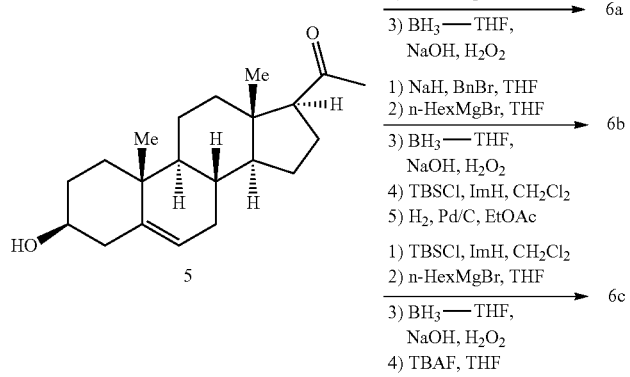

The coupling partners for these compounds can be prepared by synthetic routes. OXY133 or derivatives 6 can be acylated at the 3 and/or 6-hydroxyl with succinic anhydride, protected aspartic acid, or glycine methyl ester and the resulting carboxylic acids can then be activated as the N-hydroxy succinimide or p-nitrophenol derivatives and then coupled to alendronic acid to yield the conjugates.

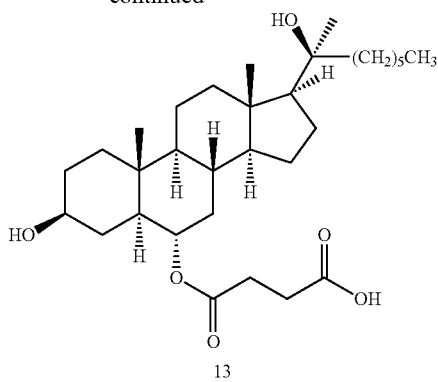

13

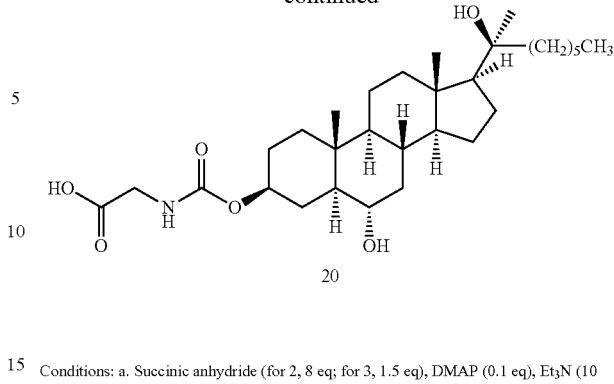

20

Conditions: a. Succinic anhydride (for 2, 8 eq; for 3, 1.5 eq), DMAP (0.1 eq), Et₃N (10 eq), DCM, room temperature, overnight; for 2, quant. for 3 aprx. 40%. b. Triphosgene (0.66 eq), pyr (5 eq), glyOMe (3 eq), DCM, room temperature, 1 hr. c. K₂CO₃, MeOH/H₂O, room temperature, overnight, quant. d. CDI (7 eq), THF, room temperature, overnight; then ALN (nBu₄N⁺)₃, DMF, room temperature, overnight; DOWEX 50WX4 100-200 Na form ~15%; e. pTsOH (0.1 eq), MeOH/DCM, room temperature, 30 min. f. Ac₂O (1.4 eq), pyr, room temperature, overnight, 58%.

6 →(b, c, e)

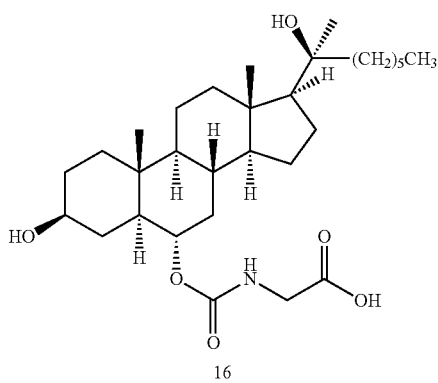

16

6 →(f, e)

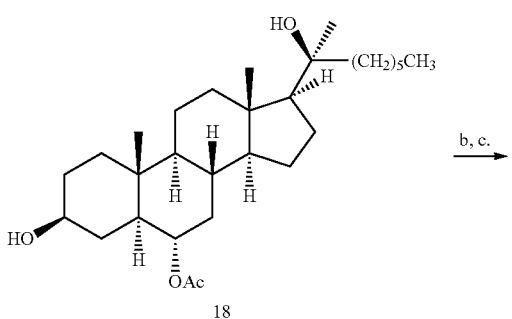

18

→(b, c)

Due to incompatible solubility profiles of ALN and activated esters intermediates, formation of the tetrabutylammonium salt of alendronic acid was essential to achieving a successful coupling reaction using DMF. Appending the extremely polar bisphosphonate moiety to Oxy133 presents unique synthetic challenges as the resulting conjugates are insoluble in organic solvents, cannot be purified by traditional normal-phase chromatography, and have surfactant-like properties. Direct amide bond formation with ALN is not possible due to competing side reactions with the phosphonic acid functions. Accordingly, ALN conjugates are formed through an isolated activated ester which is coupled to ALN under basic conditions in a separate step. The ALN salt form was manipulated and purification was performed using reverse-phase solid phase extraction (SPE) cartridges to allow for convenient preparation on a 50-100 mg scale. Use of the tetrabutylammonium salt greatly enhanced the retention of the final conjugates on the SPE cartridge. Whereas the sodium salt had essentially no retention, the tetrabutylammonium salt was eluted only with a significant amount of methanol in the mobile phase. Finally, the remaining tetrabutylammonium salt was exchanged for the sodium salt with Dowex cationic exchange resin to provide OXY-ALN conjugates suitable for biological testing.

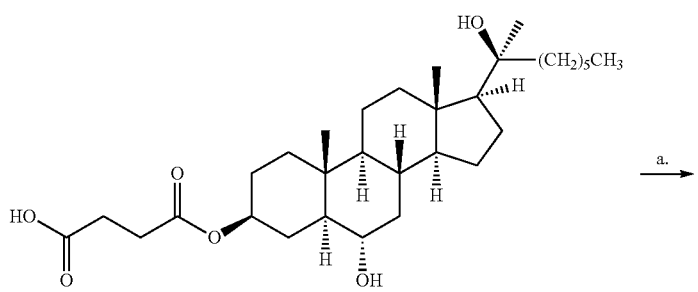

9

→ a.

-continued
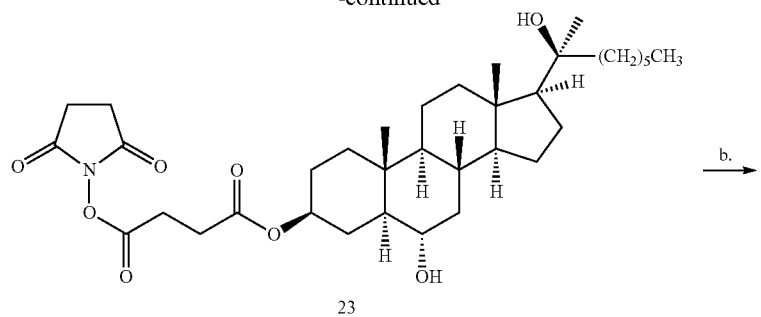
23
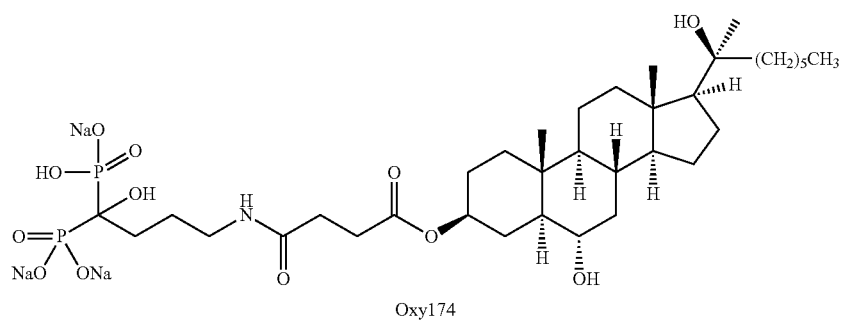
Oxy174
8 or 13 →(a, b.) Oxy166 or Oxy167
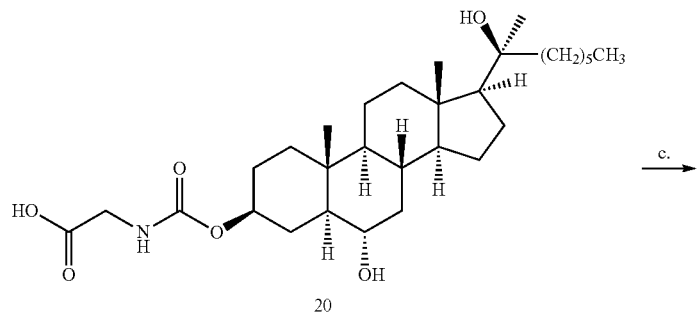
20
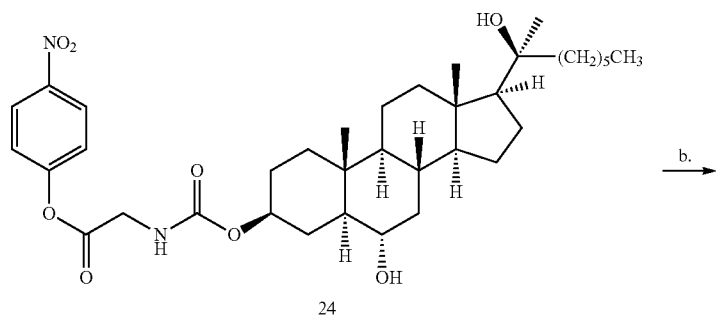
24

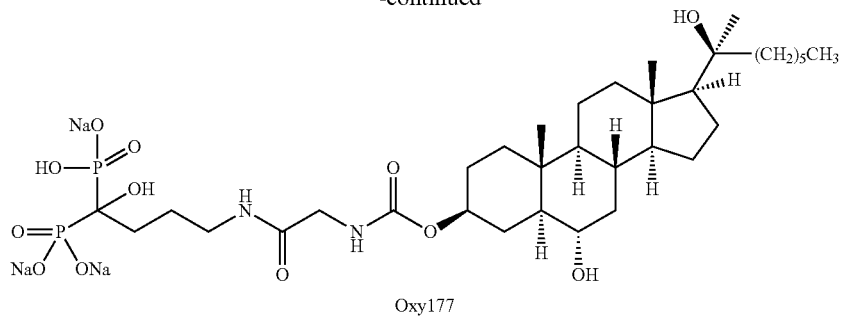

Oxy177

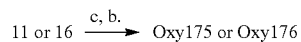

11 or 16 —c, b.→ Oxy175 or Oxy176

Conditions: a. DCC, NHS, DCM, room temperature, overnight ~70%; b) ALN (nBu₄N⁺)₃, room temperature, overnight; DOWEX 50WX4 100-200 Na form, ~50%; c) DCC, pNO₂PhOH, DCM, room temperautre, overnight, ~65%.

In another embodiment of the present invention, exhaustive acylation conditions can be used to achieve acylation of the tertiary alcohol at the 20-position and form peracylated oxysterol-bisphosphonate conjugates. An exhaustive acylation of OXY133-ALN conjugate results in an OXY133-ALN conjugate having acylation at positions 3, 6, and 20 with the same or different R groups. Below are three examples of exhaustive acylation of OXY133 with the same R groups:

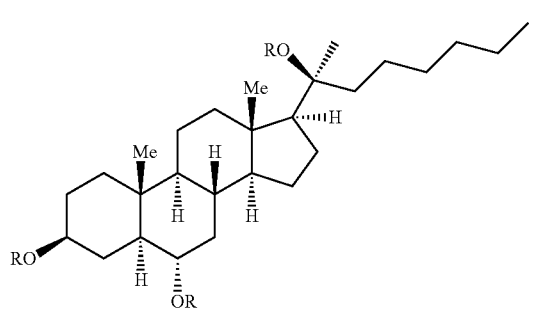

7 a, b, c

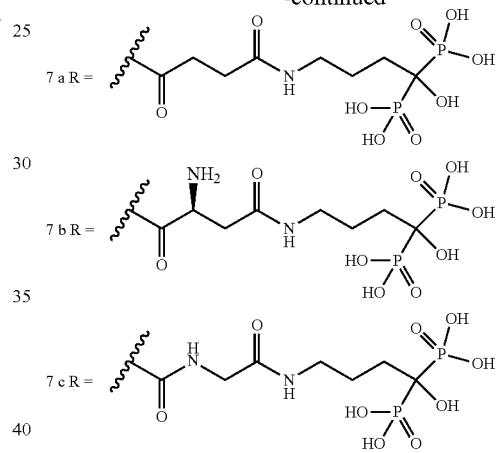

Figure 5:
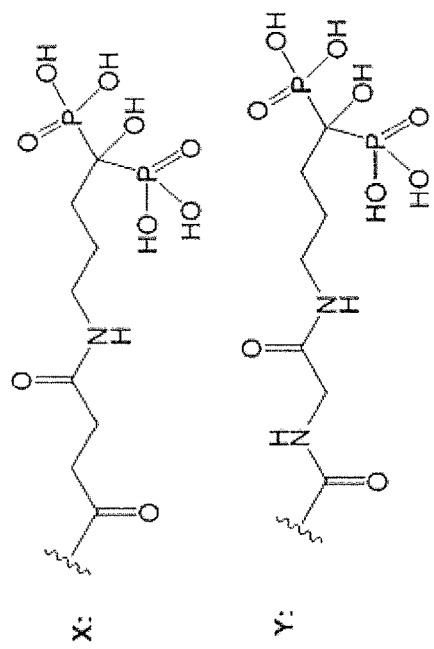
FIG. 5 shows several compounds according to the invention.
Figure 5:
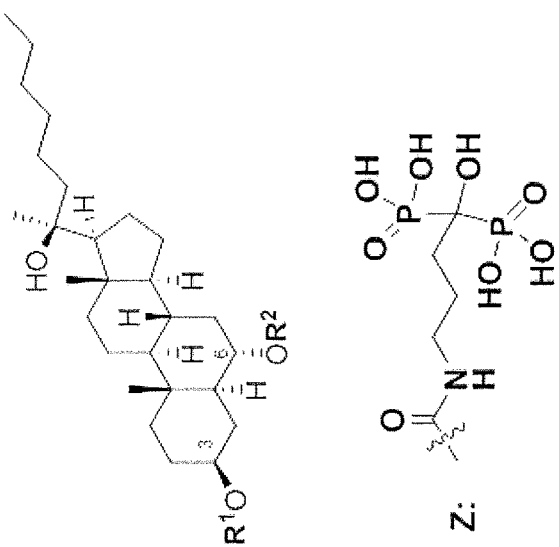

In another embodiment of the invention, OXY133-ALN conjugates have been synthesized. Examples of OXY133-ALN conjugates and their syntheses are provided below. A summary of the structures of the OXY133 and the OXY133-ALN conjugates (OXY166, OXY167, OXY174, OXY175, OXY176, OXY177, and OXY178) is provided in FIG. 5. Provided below are examples of the synthesis of specific OXY133-ALN conjugates.

EXAMPLE 1

Synthesis of Oxy166 and Intermediates

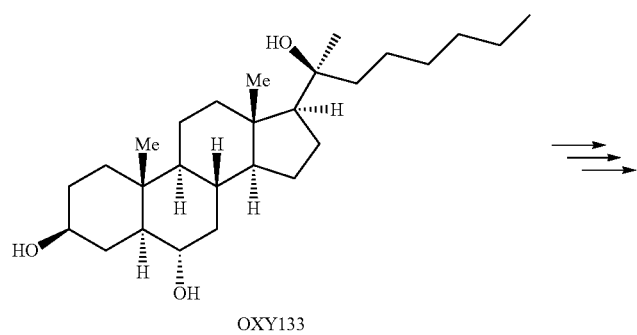

OXY133

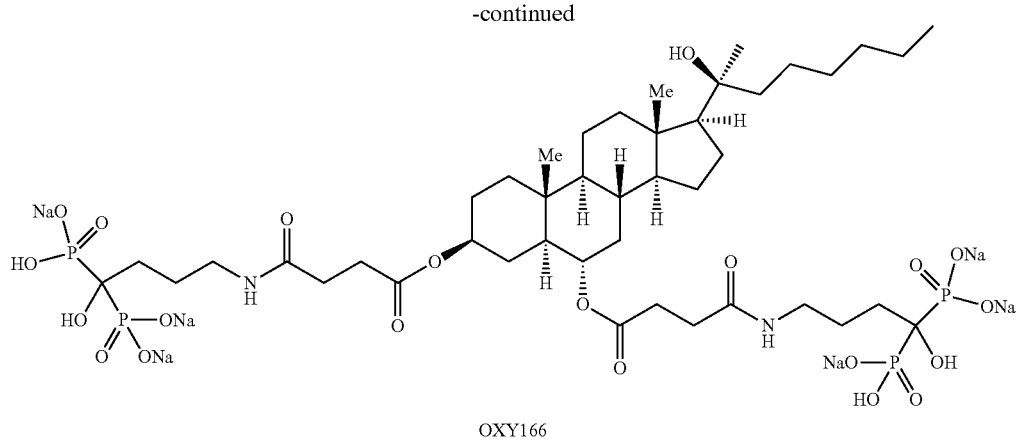

OXY166

OXY166 has succinate-linker units attached to the 3 and 6-positions of OXY133. OXY166 can be synthesized directly from OXY133 and requires no protecting group manipulation.

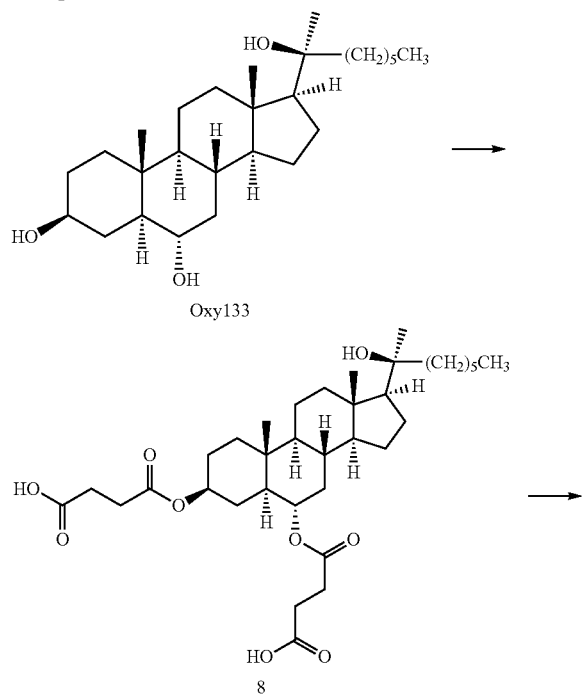

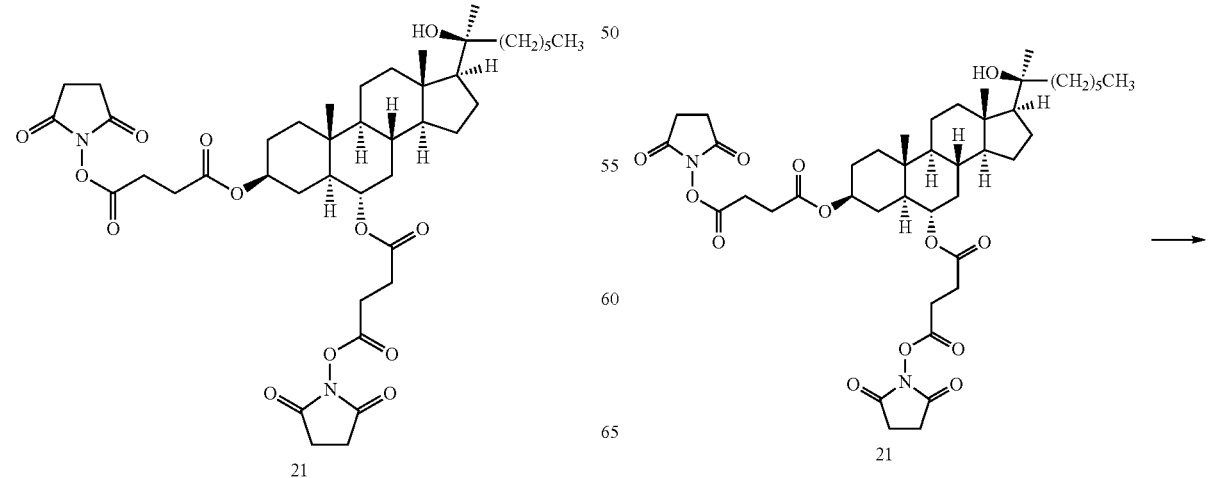

Oxy133 (236 mg, $5.61 \times 10^{-4}$ mol, 1 eq) was dissolved in 5 mL of dichloromethane with DMAP, 4-dimethylaminopyridine, (6.8 mg, $5.61 \times 10^{-5}$ mol, 0.1 eq) and triethylamine (566 mg, $5.61 \times 10^{-3}$ mol, 10 eq). Succinic anhydride (449 mg, $8.42 \times 10^{-4}$, 8 eq) was added as a solid and the mixture was stirred at room temperature overnight. In the morning, the solution was diluted in 1N aqueous HCl and extracted with dichloromethane. The combined dichloromethane portions were washed once with water then dried with $Na_2SO_4$ and concentrated to give crude 8. To crude 8 was added to N,N'-dicyclohexylcarbodiimide, DCC, (208 mg, $1.0 \times 10^{-3}$ mol, 1.8 eq) and N-hydroxysuccinimide (101 mg, $1.0 \times 10^{-3}$ mol, 1.8 eq) which was then dissolved in 2.5 mL of dichloromethane and stirred vigorously overnight. In the morning the reaction mixture was filtered, concentrated by rotary evaporation, brought up in EtOAc, filtered again and then purified by $SiO_2$ chromatography (70% EtOAc: $C_6$'s) to provide 261 mg (57% over 2 steps) of 21. $^1$H-NMR (400 MHz, $CDCl_3$): δ 4.73 (m, 2H), 2.93-2.87 (m, 4H), 2.83 (s, 8H), 2.80-2.70 (m, 4H), 2.06-1.98 (m, 2H), 1.90-1.85 (m, 1H), 1.77-1.68 (m, 2H), 1.66-1.62 (m, 1H), 1.60-1.54 (m, 1H), 1.53-1.47 (m, 3H), 1.46-1.35 (m, 3H), 1.34-1.18 (m, 13H), 1.15-0.98 (m, 4H), 0.96-0.90 (m, 1H), 0.89-0.85 (m, 6H), 0.82 (s, 3H), 0.68 (m, 1H) ppm.

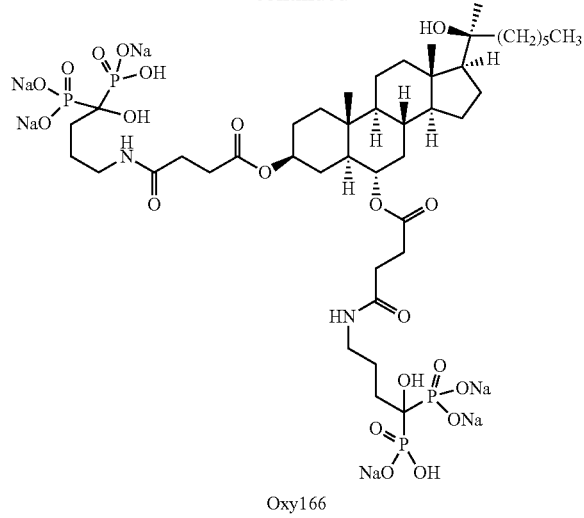

Oxy166

Intermediate 21 (45 mg, 5.49×10⁻⁵ mol, 1 eq) was dissolved in 0.3 mL anhydrous DMF to which a solution of alendronate tris-tetrabutylammonium salt prepared from alendronic acid (27 mg, 1.10×10⁻⁴ mol, 2 eq) in 0.3 mL anhydrous DMF was added. The mixture was stirred overnight at room temperature and then concentrated. Excess DMF was removed by repeatedly adding and removing toluene by rotary evaporation. This crude mixture was dissolved in water and loaded onto a 2 g C-18 solid phase extraction cartridge. The cartridge was initially eluted with a water/MeOH mixture that was gradually increased from 0 to 50% MeOH. Fractions with the desired compound were pooled, concentrated and then exchanged to the sodium salt using Dowex 50WX4 100-200 resin. Water was removed by lyophilization to yield 30 mg (approx. 45%) of Oxy166 as the sodium salt. $^1$H-NMR key resonances (500 MHz, D$_2$O): δ 4.54 (bs, 2H), 3.07 (t, 6.2 Hz, 4H), 2.51 (m, 4H), 2.42 (m, 4H), 1.94-0.64 (broad) ppm. HRMS: calc for C$_{43}$H$_{77}$N$_2$O$_{21}$P$_4$ [M−2H]$^{2-}$: 540.1951; found: 540.1576 m/z.

EXAMPLE 2

Synthesis of Oxy167 and Intermediates

OXY167 has a succinate-linker unit attached to the 6-position of OXY133. This attachment can be achieved by coupling of Oxy133 to succinic anhydride to yield an intermediate 13. Activated ester coupling to alendronic acid in aqueous media can yield compound OXY167.

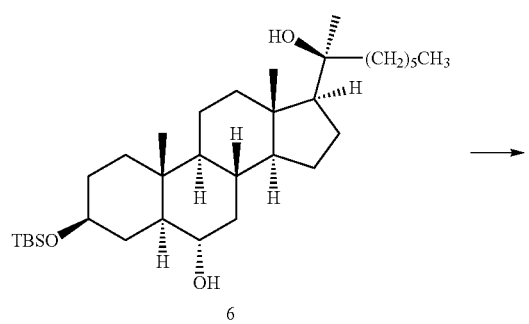

6

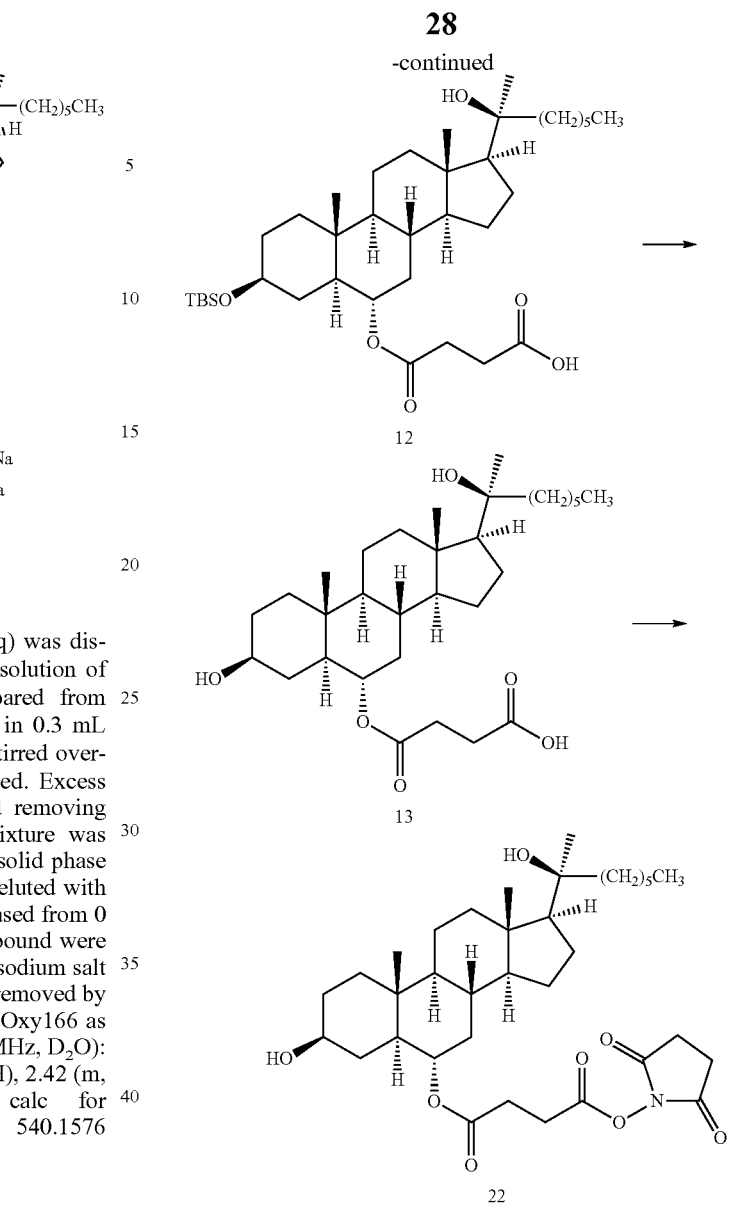

12

13

22

Intermediate 6 (300 mg, 5.61×10⁻⁴ mol, 1 eq) was dissolved in 5 mL of dichloromethane and with 4-dimethylaminopyridine, DMAP (6.8 mg, 5.61×10⁻⁵ mol, 0.1 eq) and triethylamine (283 mg, 2.24×10⁻³ mol, 5 eq). Succinic anhydride (84 mg, 8.42×10⁻⁴, 1.5 eq) was added as a solid and the mixture was stirred at room temperature overnight. In the morning, the solution was diluted in 1N aqueous HCl and extracted with dichloromethane. The combined dichloromethane portions were washed once with water then dried with Na$_2$SO$_4$ and concentrated to give 365 mg of crude 12. The crude 12 was dissolved in 2 mL of a 1:1 mixture of DCM:MeOH to which para-toluenesulfonic acid monohydrate (11 mg, 5.61×10⁻⁵ mol, 0.1 eq) was added as a solid and the reaction was stirred for 30 min at room temperature. 20 mL of sat. NaCO$_3$H aqueous solution was added and then extracted with ethyl acetate. The combined organic fractions were dried over Na$_2$SO$_4$, concentrated to yield crude 13 which was used without further purification. To crude 13 was added to N,N'-dicyclohexylcarbodiimide, DCC, (208 mg, 1.0×10⁻³ mol, 1.8 eq) and N-hydroxysuccinimide (101 mg, 1.0×10⁻³ mol, 1.8 eq) which was then dissolved in 2.5 mL of dicholoromethane and stirred vigorously overnight. In the morning the reaction mixture was filtered, concentrated by rotary evaporation, brought up in EtOAc, filtered again and then purified by SiO$_2$ chromatography (70% EtOAc: C$_6$'s) to provide 98 mg (28% over 3 steps) of 22. $^1$H-NMR (400 MHz, CDCl$_3$): δ (key resonances): 4.69 (ddd, 10.8 Hz, 10.8 Hz, 4.8 Hz, 1H), 3.52 (dddd, 10.8 Hz, 10.8 Hz, 4.8 Hz, 4.8 Hz, 1H), 2.61 (m, 2H), 2.60 (2, 4H), 2.56 (m, 2H) ppm.

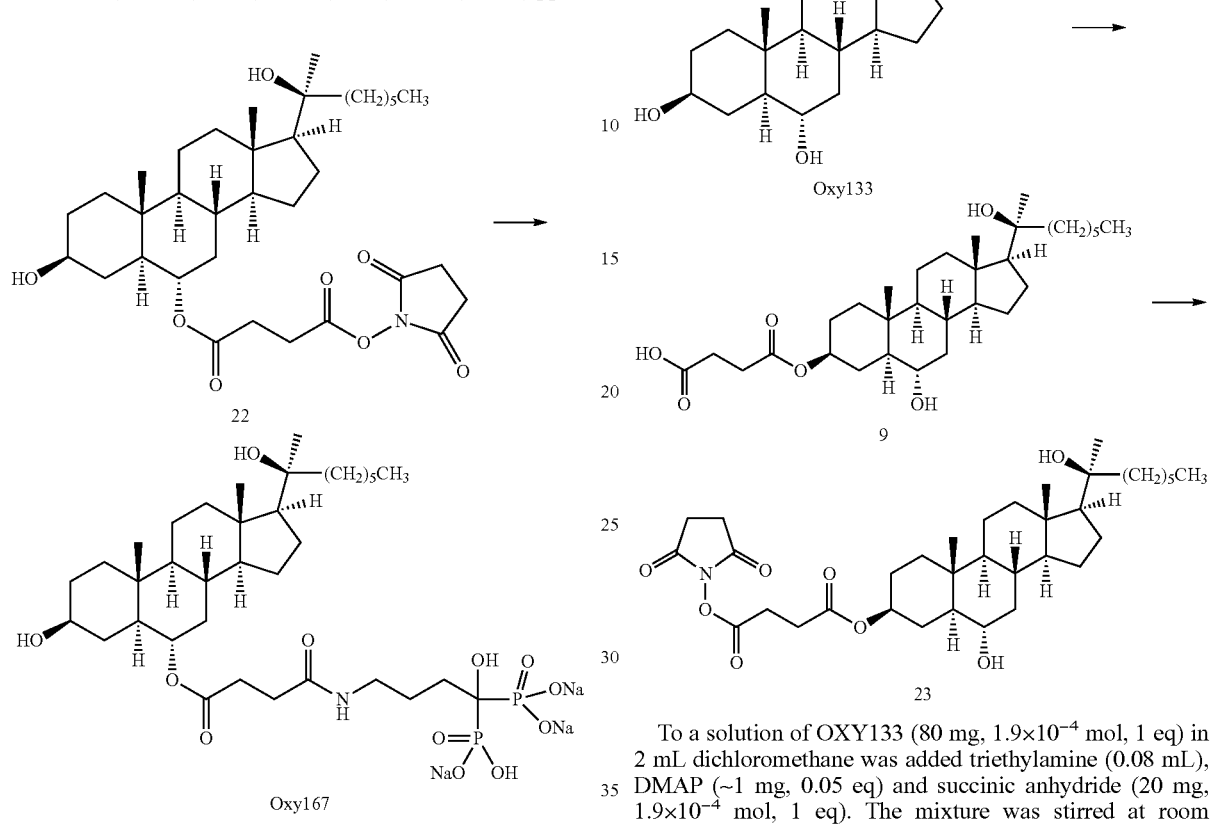

Intermediate 22 (50 mg, 8.09×10$^{-5}$ mol, 1 eq) was dissolved in 0.3 mL anhydrous DMF to which a solution of alendronate tris-tetrabutylammonium salt prepared from alendronic acid (20 mg, 8.09×10$^{-5}$ mol, 1 eq) in 0.3 mL anhydrous DMF was added. The mixture was stirred overnight at room temperature and then concentrated. Excess DMF was removed by repeatedly adding and removing toluene by rotary evaporation. This crude mixture was dissolved in water and loaded onto a 2 g C-18 solid phase extraction cartridge. The cartridge was initially eluted with a water/MeOH mixture that was gradually increased from 0 to 50% MeOH. Fractions with the desired compound were pooled, concentrated and then exchanged to the sodium salt using Dowex 50WX4 100-200 resin. Water was removed by lypholization to yield 33 mg (approx. 50%) of Oxy167 as the sodium salt. $^1$H-NMR key resonances (500 MHz, D$_2$O): δ 4.60 (bs, overlapping with HDO), 3.41 (bs, 1H), 3.08 (bs, 2H), 2.59-2.35 (m, 4H), 2.01-0.56 (broad) ppm. HRMS: calc for C$_{35}$H$_{62}$NO$_{12}$P$_2$ [M-H]$^-$: 750.3753; found: 750.3149 m/z.

EXAMPLE 3

Synthesis of Oxy174 and Intermediates

OXY174 has a succinate-linker unit attached to the 3-position of OXY133. OXY174 is synthesized by reacting OXY133 with succinic anhydride to yield intermediate 10 which is activated as the N-hydroxy succinimide ester, 23, prior to reaction with alendronate tetra-n-butyl ammonium salt.

To a solution of OXY133 (80 mg, 1.9×10$^{-4}$ mol, 1 eq) in 2 mL dichloromethane was added triethylamine (0.08 mL), DMAP (~1 mg, 0.05 eq) and succinic anhydride (20 mg, 1.9×10$^{-4}$ mol, 1 eq). The mixture was stirred at room temperature for six hours after which a second portion of succinic anhydride was added (20 mg, 1 eq). After 18 hours at room temperature, the reaction mixture was diluted with saturated NaHCO$_3$ solution (20 mL) and dichloromethane (10 mL). The layers were separated and the aqueous layer extracted with dichloromethane (3×10 mL). The combined organic layers were washed with 0.5 M HCl solution and water, dried over Na$_2$SO$_4$ and the solvent evaporated. The crude product was purified by silica gel chromatography (EtOAc, then 10% MeOH in EtOAc) to afford a fraction rich in recovered staring material, a fraction rich in desired 9 (40 mg, 38%) and mixed fractions. $^1$H-NMR (CDCl$_3$, 300 MHZ) δ: 4.71 (1H, dddd, J=11.2, 11.2, 4.4, 4.4 Hz), 3.36 (1H, ddd, J=10.8, 10.8, 4.4 Hz), 2.65 (4H, m), 2.19 (1H, m), 2.10-1.90 (3 H, m), 1.85-1.60 (7 H, m), 1.55-1.38 (7H, m), 1.25 (11H, brs), 1.20-0.95 (4 H, m), 0.90 (3H, m), 0.86 (3H, s), 0.80 (3H, s) 0.62 (2H, m) ppm.

To a solution of crude 9 (520 mg, 1.0×10-3 mol., 1 eq) in dichloromethane (6 mL) and N-hydroxysuccinimide (230 mg, 2.0×10-3 mol, 2 eq) was added solid N,N'-dicyclohexylcarbodiimide, DCC (412 mg, 2.0×10-3 mol, 2 eq.) in one portion. The mixture was stirred at room temperature for six hours after which the solvent was removed by evaporation. The mixture was re-suspended in EtOAc (20 mL) and filtered. Purification by silica gel chromatography (hexane, EtOAc, gradient) afforded the desired product 23 (least-polar fraction 240 mg, 38%), an isomeric product (medium polar fraction 90 mg, 14%) and recovery of Oxy133 (polar fraction 150 mg, 35%). 1H-NMR (CDCl$_3$, 300 MHz) δ: 4.71 (1H, dddd, J=11.2, 11.2, 4.4, 4.4 Hz), 3.40 (1H, ddd, J=10.8, 10.8, 4.4 Hz), 3.92 (2H, m), 2.79 (4H, s), 2.62 (2H, m), 2.19 (1H, m), 2.10-1.90 (3 H, m), 1.85-1.60 (7 H, m), 1.55-1.38

(7H, m), 1.25 (11H, brs), 1.20-0.95 (4 H, m), 0.90 (3H, m), 0.86 (3H, s), 0.80 (3H, s) 0.62 (2H, m) ppm.

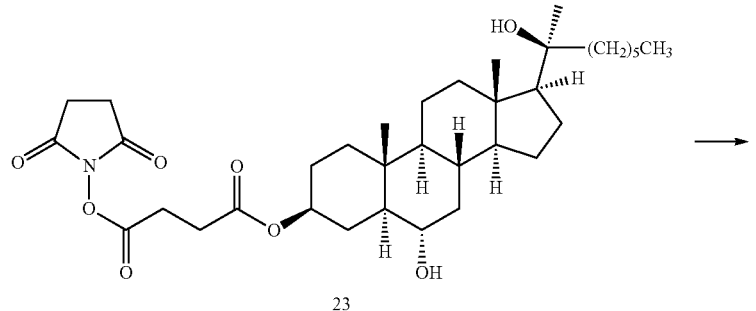

23

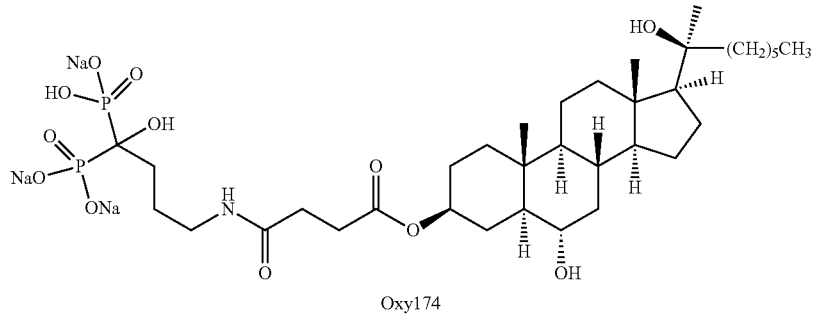

Oxy174

Oxy 174 was synthesized from 23 (110 mg, $1.8 \times 10^{-4}$ mol, 1 eq) following the procedure for the synthesis of Oxy167 to afford after lyophilization 35 mg (24%) of Oxy174. HRMS: calc for $C_{35}H_{62}NO_{12}P_2$ [M-H]$^-$: 750.3753; found: 750.3741 m/z.

Due to incompatible solubility profiles of ALN and activated esters intermediates, such as 23, formation of the tetrabutylammonium salt of alendronic acid was essential to achieving a successful coupling reaction using DMF. Appending the extremely polar bisphosphonate moiety to Oxy133 presents unique synthetic challenges as the resulting conjugates are insoluble in organic solvents, cannot be purified by traditional normal-phase chromatography, and have surfactant-like properties. The ALN salt form was manipulated and purification was performed using reverse-phase solid phase extraction (SPE) cartridges to allow for convenient preparation on a 50-100 mg scale. Use of the tetrabutylammonium salt greatly enhanced the retention of the final conjugates on the SPE cartridge. Whereas the sodium salt had essentially no retention, the tetrabutylammonium salt was eluted only with a significant amount of methanol in the mobile phase. Finally, the remaining tetrabutylammonium salt was exchanged for the sodium salt with Dowex cationic exchange resin to provide OXY174 suitable for biological testing.

EXAMPLE 4

Synthesis of Oxy175 and Intermediates

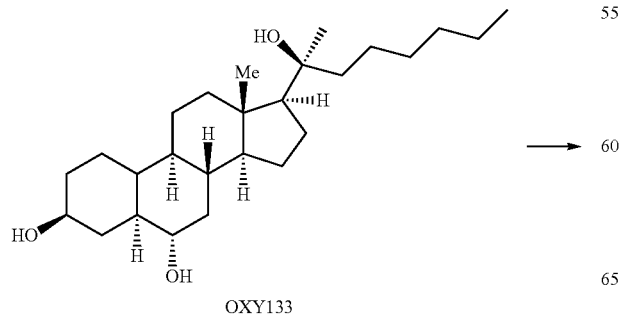

OXY133

-continued

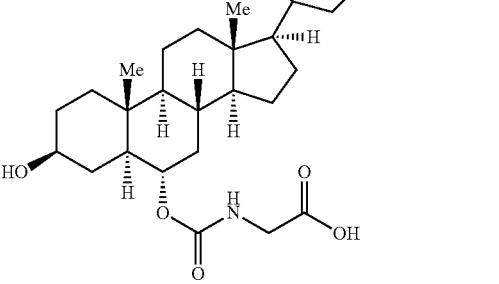

16

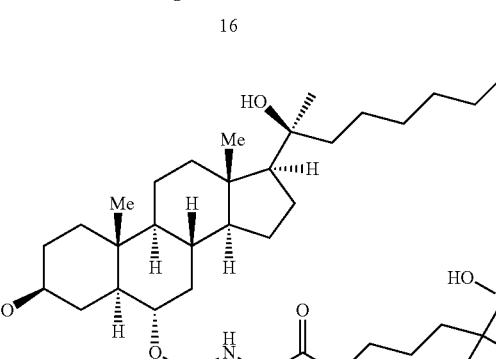

OXY175

OXY175 has a carbamate-linker unit attached to the 6-position of OXY133. Direct amide bond formation with ALN is not possible due to competing side reactions with the phosphonic acid functions. Accordingly, ALN conjugates are formed through an isolated activated ester which is coupled to ALN under basic conditions in a separate step.

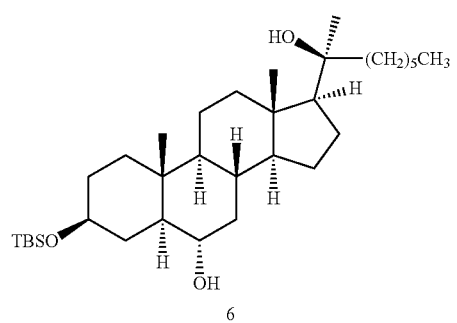

6

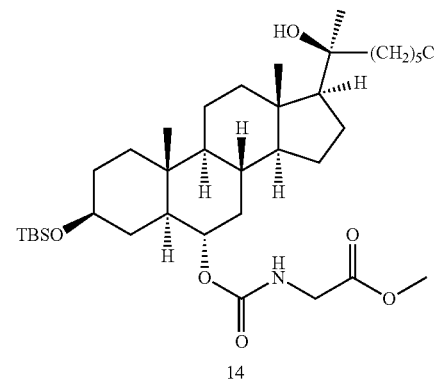

14

The synthesis of OXY175 began with 6, where 6 (315 mg, 5.89×10⁻⁴ mol, 1 eq) is combined with triphosgene (58 mg, 1.96×10⁻⁴ mol, ⅓ eq) in 3 mL of anhydrous THF and stirred at room temperature. Pyridine (232 mg, 2.9×10⁻³, 5 eq) is added at once by syringe and the reaction mixture was stirred for 15 min at room temperature. Glycine methyl ester HCL (151 mg, 1.20×10⁻⁴ mol, 2 eq) was dissolved in 1M aqueous NaOH which was extracted with dichloromethane, dried over $Na_2SO_4$ and concentrate by rotary evaporation. The resulting free amine was dissolved in 1 mL of anhydrous THF and added to the reaction mixture by syringe. After 1 hr the reaction was quenched with 1 M aqueous HCl, extracted with ethyl acetate, dried with $Na_2SO_4$, concentrated and purified by $SiO_2$ chromatography (20% EtOAc: $C_6$'s) to provide 194 (51%) mg of 14 as a white foam. ¹H-NMR (500 MHz, CDCl₃): δ 5.12 (dd, ~5.2 Hz, ~5.5 Hz, 1H), 4.53 (ddd, 10.8 Hz, 10.8 Hz, 4.5 Hz, 1H), 3.98 (dd, 18.5 Hz, 5.5 Hz, 1H), 3.92 (dd, 18.5 Hz, 5.2 Hz, 1H), 3.74 (s, 3H), 3.48 (dddd, 10.3 Hz, 10.3 Hz, 4.8 Hz, 4.8 Hz, 1H), 2.03 (m, 2H), 1.79-1.56 (m, 6H), 1.53-1.37 (m, 5H), 1.36-1.07 (m, 18H), 1.05-0.93 (m, 3H), 0.91-0.86 (m, 3H), 0.86 (s, 9H), 0.83 (s, 3H), 0.80 (s, 3H), 0.62 (m, 1H), 0.26 (s, 6H) ppm.

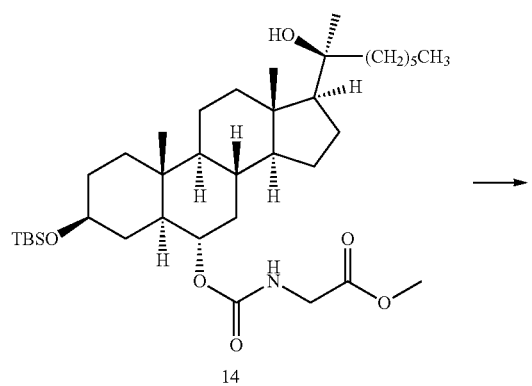

14

-continued

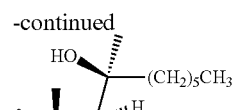

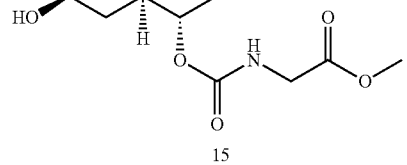

15

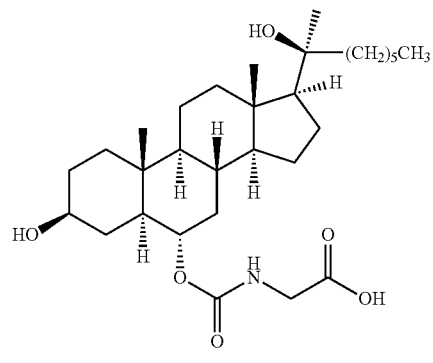

16

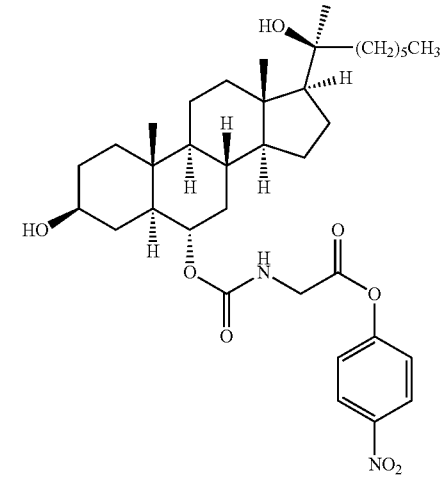

25

Intermediate 14 (194 mg, 2.98×10⁻⁴ mol, 1 eq) is dissolved in 3 mL of MeOH and para-toluenesulfonic acid monohydrate (5.6 mg, 2.98×10⁻⁵ mol, 0.1 eq) was added as a solid and the mixture was stirred at room temperature for 30 mm. 20 mL of sat. $NaCO_3H$ aqueous solution was added and then extracted with ethyl acetate. The combined organic fractions were dried over $Na_2SO_4$, concentrated to yield 158 mg of 15 as a white foam which was used without further purification. 15 (64 mg, 1.19×10⁻⁴ mol, 1 eq) was dissolved in 2 mL of 9:1 MeOH: $H_2O$ solution to which $K_2CO_3$ (66 mg, $4.76 \times 10^{-4}$, 4 eq) was added as a solid. The reaction mixture was stirred overnight at room temperature, quenched with 1N aqueous HCl and extracted into EtOAc which was dried over $Na_2SO_4$ concentrated to give 60 mg of crude 16 which was used without further purification. To 16 (60 mg, $1.15 \times 10^{-4}$ mol) was added solid N,N'-dicyclohexylcarbodiimide, DCC, (27 mg, $1.31 \times 10^{-4}$ mol, 1.1 eq) in a round bottom flask to which a solution of para-nitrophenol (22 mg, $1.55 \times 10^{-4}$ mol, 1.3 equivalents) in 2 mL of DCM was added at once and the mixture was stirred at room temperature overnight. The reaction mixture was filtered, concentrated, dissolved in EtOAc and then filtered again. Upon concentration the residue was purified by $SiO_2$ chromatography (50% EtOAc: $C_6$'s) to yield 46 mg (62% over 3 steps) of 25 as a colorless oil. $^1$H-NMR (500 MHz, $CDCl_3$): δ 8.25 (d, 9.1 Hz, 2H), 7.30 (d, 9.1 Hz, 2H), 5.40 (t, 5.7 Hz, 1H), 4.58 (m, 1H), 4.21 (d, 5.7 Hz, 2H), 3.49 (m, 1H), 2.06-1.99 (m, 2H), 1.98-1.84 (m, 3H), 1.81-1.75 (m, 2H), 1.72-1.67 (m, 2H), 1.64-1.45 (m, 4H), 1.44-1.34 (m, 3H), 1.33-1.17 (m, 17 H), 1.15-1.06 (m, 2H), 1.06-0.96 (m, 2H), 0.93-0.88 (m, 1H), 0.87-0.82 (m, 6H), 0.80 (s, 3H), 0.62 (m, 1H) ppm.

That is, the addition of the carbamate linker and deprotection of C-3 alcohol yielded intermediate 15. Intermediate 15 was saponified and was activated with p-nitrophenol to provide shelf-stable activated ester 25 which gave an ALN amide alpha to an NH-carbonyl upon reaction with alendronate tetra-n-butyl ammonium salt (Oxy175).

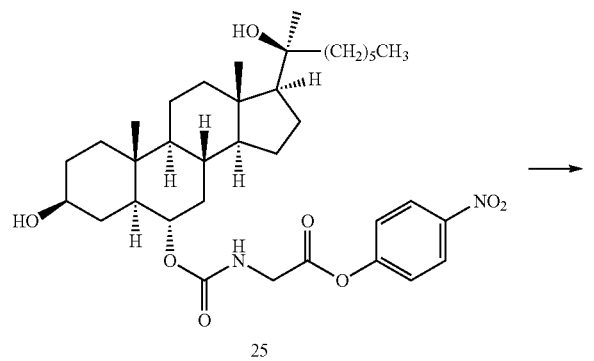

25

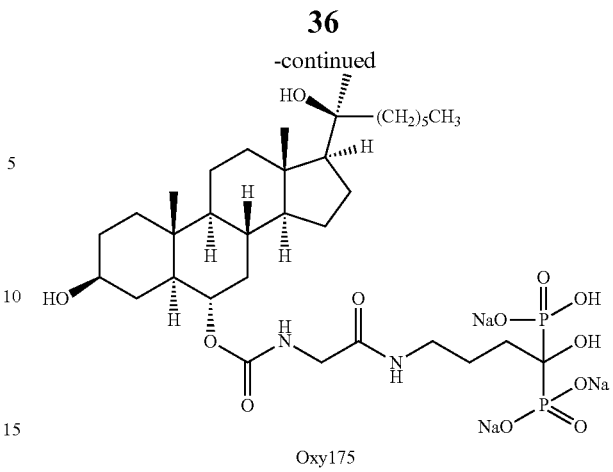

Oxy175

Intermediate 25 (43 mg, $6.7 \times 10^{-5}$ mol, 1 eq) was dissolved in 0.3 mL anhydrous DMF to which a solution of alendronate tris-tetrabutylammonium salt prepared from alendronic acid (17 mg, $6.7 \times 10^{-5}$ mol, 1 eq) in 0.3 mL anhydrous DMF was added. The mixture was stirred overnight at room temperature and then concentrated. Excess DMF was removed by repeatedly adding and removing toluene by rotary evaporation. This crude mixture was dissolved in water and loaded onto a 2 g C-18 solid phase extraction cartridge. The cartridge was initially eluted with a water MeOH mixture that was gradually increased from 0 to 50% MeOH. Fractions with the desired compound were pooled, concentrated and then exchanged to the sodium salt using Dowex 50WX4 100-200 resin. Water was removed by lypholization to yield 25 mg (approx. 44%) of Oxy175 as the sodium salt. $^1$H-NMR key resonances (500 MHz, $D_2O$): δ 4.46 (bs, 1H), 3.77 (bs, 1H), 3.63 (bs, 1H), 3.41 (bs, 1H), 3.12 (bs, 2H), 2.24-0.13 (broad) ppm. HRMS: calc for $C_{34}H_{61}NO_{12}P_2$ [M-H]$^-$: 751.3705; found: 751.3367 m/z.

EXAMPLE 5

Synthesis of Oxy176 and Intermediates

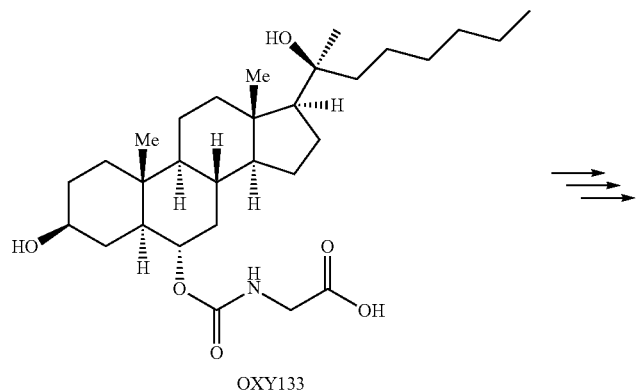

OXY133

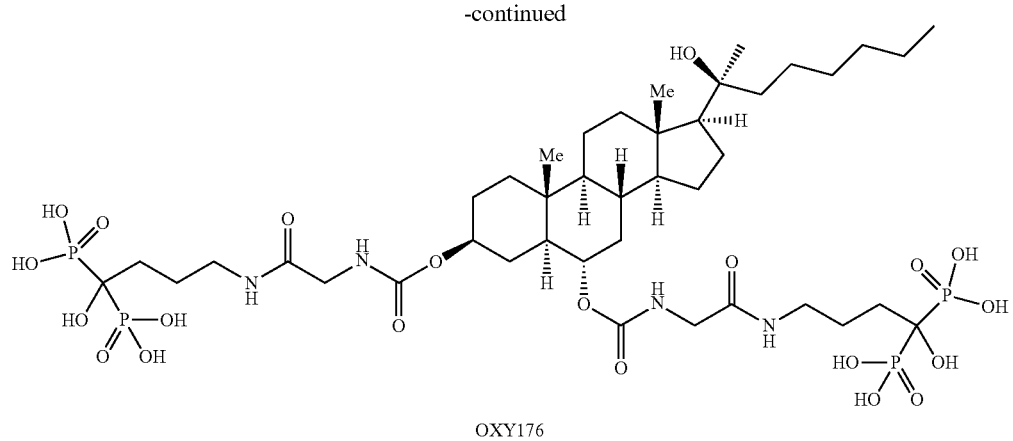
OXY176
OXY176 has carbamate-linker units attached to the 3 and 6-positions of OXY133. OXY176 can be synthesized directly from OXY133.
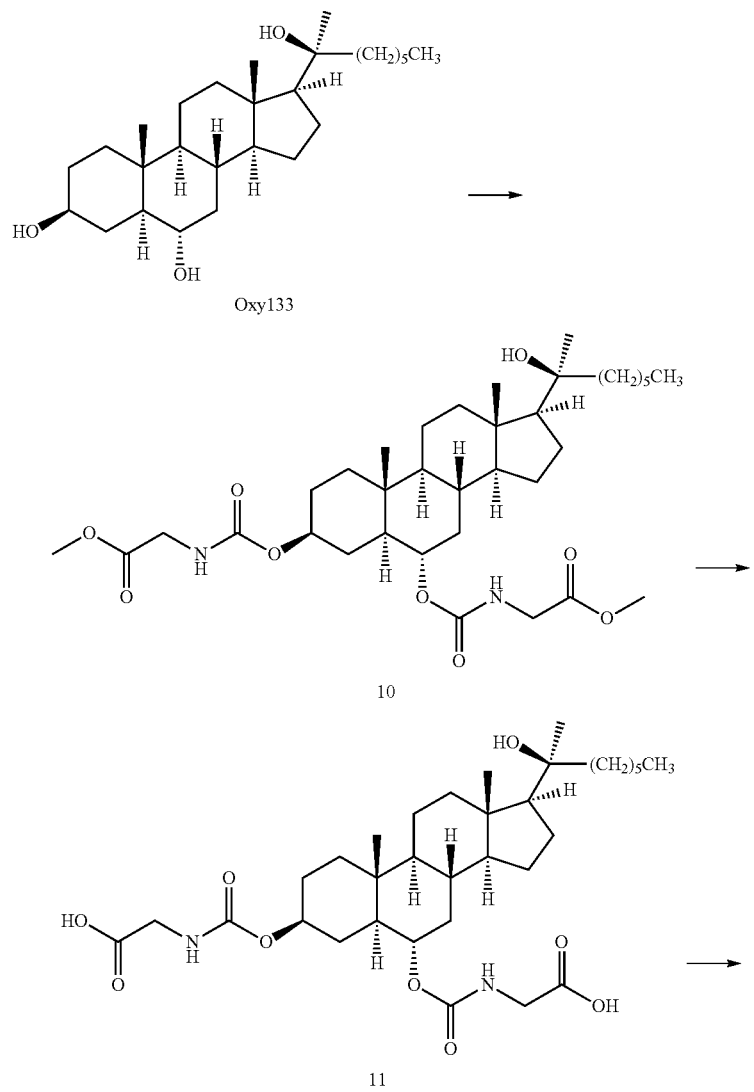

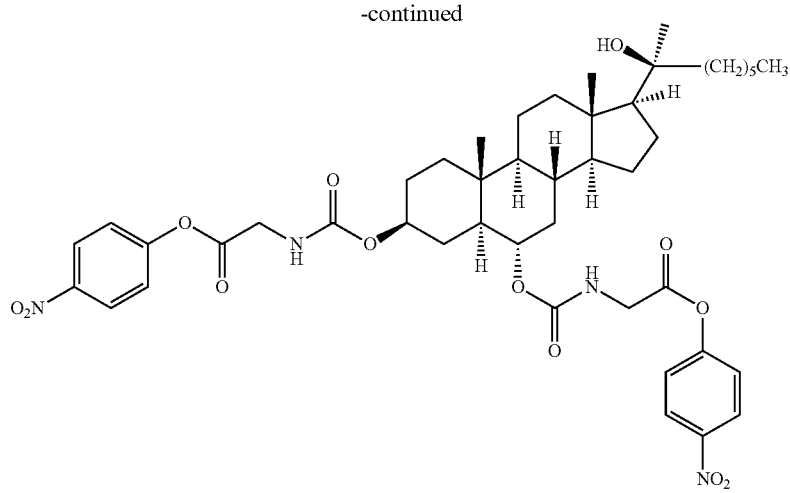

26

Oxy133 (300 mg, 7.14×10⁻⁴ mol, 1 eq) and triphosgene (141 mg, 4.76×10⁻⁴ mol, ⅔ eq) in 4 mL of anhydrous THF and stirred at room temperature. Pyridine (232 mg, 2.9×10⁻³, 5 eq) is added at once by syringe and the reaction mixture was stirred for 15 min. Glycine methyl ester HCL (269 mg, 2.14×10⁻³ mol, 3 eq) was dissolved in 1M aqueous NaOH which was extracted with dichloromethane, dried over Na₂SO₄ and concentrate by rotary evaporation. The resulting free amine was dissolved in 1 mL of anhydrous THF and added to the reaction mixture by syringe. After 1 hr the reaction was quenched with 1 M aqueous HCl, extracted with ethyl acetate, dried with Na₂SO₄, concentrated and purified by SiO₂ chromatography (50% EtOAc: C₆'s) to provide 130 mg (approx. 28%) of 10 as an oil that contained some mono-functionalized compound and was used without further purification. 10 (approx. 130 mg, 2.0×10⁻⁴ mol, 1 eq) was dissolved in 2 mL of MeOH: H₂O (9:1) to which K₂CO₃ (165 mg, 1.2×10⁻⁴, 6 eq) was added as a solid. The mixture was stirred at room temperature overnight, quenched with 1N aqueous HCl, extracted with ethyl acetate, dried over Na₂SO₄ and concentrated to give crude 11. 11 (approx. 100 mg, 1.60×10⁴ mol, 1 eq) was combined with solid N,N'-dicyclohexylcarbodiimide, DCC, (73 mg, 3.53×10⁻⁴ mol, 2.2 eq) in a round bottom flask. To this mixture was added a solution of para-nitrophenol (56 mg, 4.0×10⁻⁴ mol, 2.5 equivalents) in 2 mL of anhydrous DCM which was stirred vigorously at room temperature overnight. In the morning, the mixture was filtered, DCM was removed by rotary evaporation, the mixture was suspended in EtOAc, filtered, concentrated and purified by SiO₂ chromatography to yield 30 mg (~18%) of the desired 26. ¹H-NMR (500 MHz, CDCl₃): δ 8.24 (d, 9.2 Hz, 4H), 7.30 (d, 9.2 Hz, 4H), 5.31 (m, 1H), 5.22 (m, 1H), 4.59 (m, 2H), 4.20 (m, 4H), 2.06-1.98 (m, 2H), 1.90-1.85 (m, 1H), 1.77-1.68 (m, 2H), 1.66-1.62 (m, 1H), 1.60-1.54 (m, 1H), 1.53-1.47 (m, 3H), 1.46-1.35 (m, 3H), 1.34-1.18 (m, 13H), 1.15-0.98 (m, 4H), 0.96-0.90 (m, 1H), 0.89-0.85 (m, 6H), 0.82 (s, 3H), 0.68 (m, 1H) ppm.

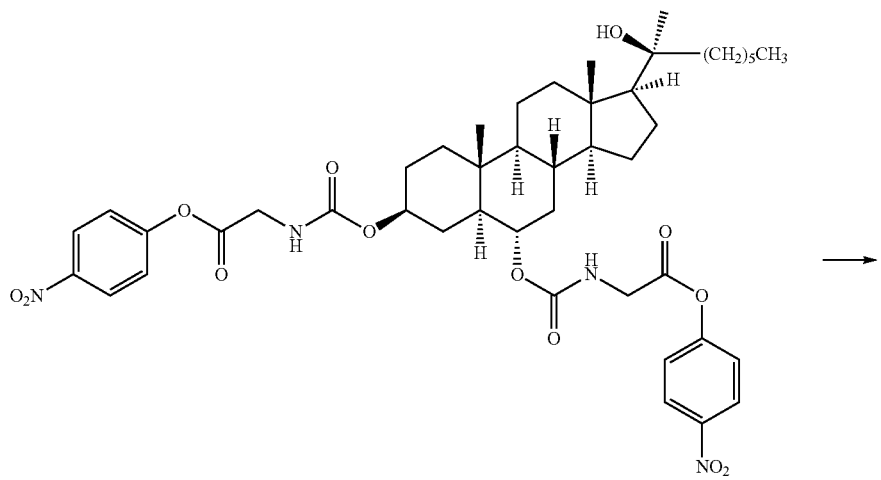

26

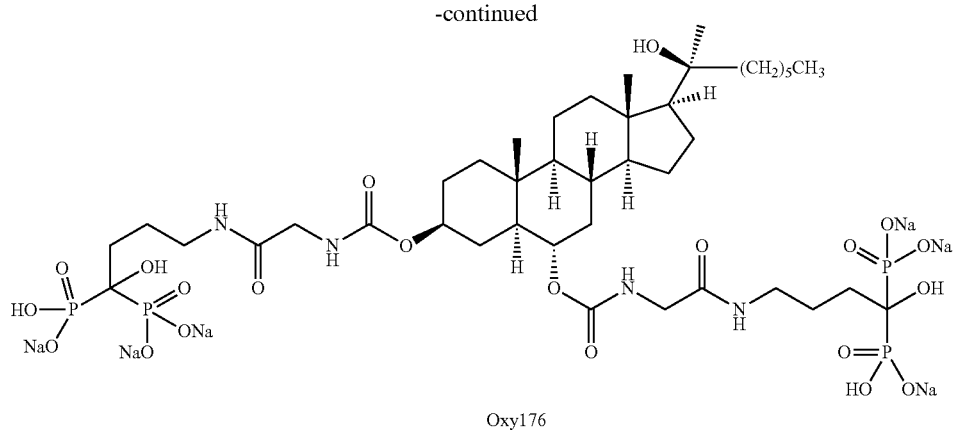

Oxy176

Oxy176 was prepared analogously to Oxy166 from 23. $^1$H-NMR key resonances (500 MHz, D$_2$O): δ 4.40 (bs, 2H), 3.70 (m, 4H), 3.12 (m, 4H), 2.01-0.55 (broad) ppm. HRMS: calc for C$_{41}$H$_{75}$N$_4$O$_{21}$P$_2$ [M-H]$^-$: 1083.3380; found: 1083.3754 m/z.

EXAMPLE 6

Synthesis of Oxy177 and Intermediates

OXY177 has a carbamate-linker unit attached to the 3-position of OXY133. TBS is removed after the acylation of the C6-hydroxyl to yield intermediate 18. The carbamate is then formed with glycine methyl ester to yield 19 which is saponified and activated as the para-nitrophenol ester 24. 24 provide Oxy177 upon reaction with alendronate tetra-n-butyl ammonium salt.

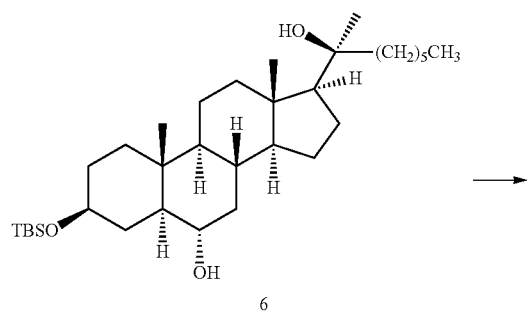

6

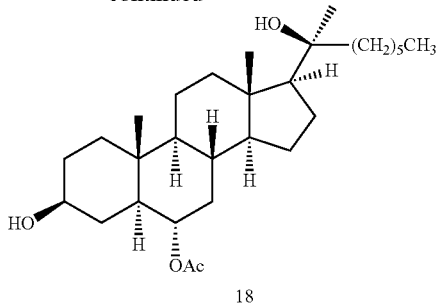

18

Intermediate 6 (330 mg, 6.17×10$^{-4}$ mol, 1 eq) was dissolved in 0.6 mL anhydrous pyridine to which acetic anhydride (88 mg, 8.64×10$^{-4}$ mol, 1.4 eq) was added and the mixture was stirred at room temperature overnight. The reaction was diluted in 1N aqueous HCl, extracted with a 50:50 mixture of ether and hexanes, dried over Na$_2$SO$_4$, concentrated by rotary evaporation and purified by SiO$_2$ chromatography to provide 206 mg (58%) of 17. 17 (206 mg, 3.57×10$^{-4}$ mol, 1 eq) is dissolved in 2 mL of MeOH:DCM 1:1 and para-toluenesulfonic acid monohydrate (7 mg, 3.57×10$^{-5}$ mol, 0.1 eq) was added as a solid and the mixture was stirred at room temperature for 30 min. 20 mL of sat. NaCO$_3$H aqueous solution was added and then extracted with ethyl acetate. The combined organic fractions were dried over Na$_2$SO$_4$, concentrated and purified by SiO$_2$ (50% EtOAc: C$_6$'s) to yield 102 mg (62%) of 18 as a white foam. $^1$H-NMR (500 MHz, CDCl$_3$): δ 4.66 (ddd, 10.8 Hz, 10.8 Hz, 4.3 Hz, 1H), 3.53 (m, 1H), 2.05 (m, 1H), 2.02 (s, 3H), 2.01 (m, 1H), 1.86 (m, 1H), 1.80 (m, 1H), 1.71 (m, 2H), 1.67-1.60 (m, 1H), 1.59-1.47 (m, 4H), 1.46-1.35 (m, 3H), 1.34-1.19 (m, 14H), 1.18-1.08 (m, 4H), 1.06-0.97 (m, 2H), 0.92-0.84 (m, 6H), 0.82 (s, 3H), 0.66 (m, 1H) ppm.

17 →

18 →

-continued

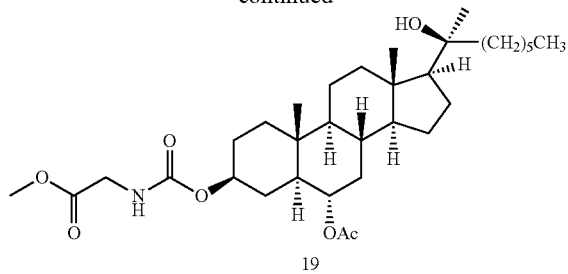

19

Intermediate 19 was prepared from 18 following the procedure for the synthesis of 15. ¹H-NMR (500 MHz, CDCl₃): δ 5.08 (t, 5.3 Hz, 1H), 4.66 (ddd, 10.7 Hz, 10.7 Hz, 4.7 Hz, 1H), 4.56 (m, 1H), 3.96 (d, 5.5 Hz, 1H), 3.75 (s, 3H), 2.06 (m, 1H), 2.02 (s, 3H), 1.97 (m, 1H), 1.87 (m, 2H), 1.72 (m, 2H), 1.64 (m, 1H), 1.60 (s, 1H), 1.56 (m, 1H), 1.50 (m, 2H), 1.46-1.40 (m, 2H), 1.32-1.21 (m, 15H), 1.67-0.99 (m, 5H), 0.93-0.85 (m, 7H), 0.82 (s, 3H), 0.68 (m, 1H) ppm.

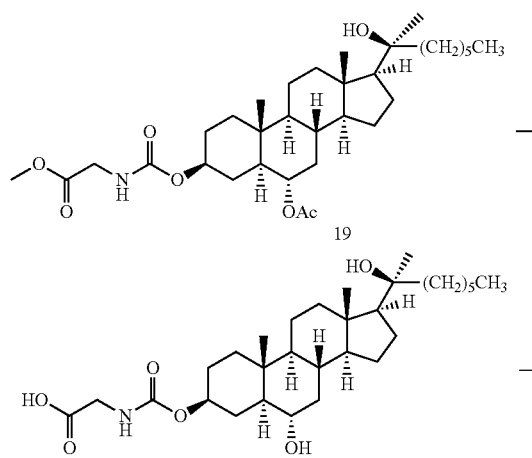

Intermediate 19 (37 mg, 6.4×10−5 mol, 1 eq) was dissolved in 1 mL of MeOH: H₂O (1:1) and 35 mg of solid K₂CO₃ was added and the mixture was stirred at room temperature overnight. The reaction mixture was diluted in 1N aqueous HCl and then extracted with EtOAc, dried and concentrated to give crude 20 which was used without further purification. 24 was synthesized from 22 according to the procedure for the synthesis of 24 to give 23 mg (53% for 2 steps). ¹H-NMR (500 MHz, CDCl₃): δ 8.27 (d, 9.1 Hz, 2H), 7.31 (d, 9.1 Hz, 2H), 5.23 (t, 5.7 Hz, 1H), 4.60 (dddd, 10.9 Hz, 10.9 Hz, 4.6 Hz, 4.6 Hz, 1H), 4.23 (d, 5.7 Hz, 2H), 3.39 (ddd, 10.8 Hz, 10.8 Hz, 4.5 Hz, 1H), 2.26 (m, 1H), 2.05 (m, 1H), 1.99 (m, 1H), 1.88 (m, 1H), 1.74-1.67 (m, 3H), 1.65-1.59 (m, 2H), 1.53-1.41 (m, 5H), 1.34-1.22 (m, 14H), 1.17 (m, 2H), 1.11-1.01 (m, 4H), 0.89-0.84 (m, 8H), 0.67 (m, 1H) ppm.

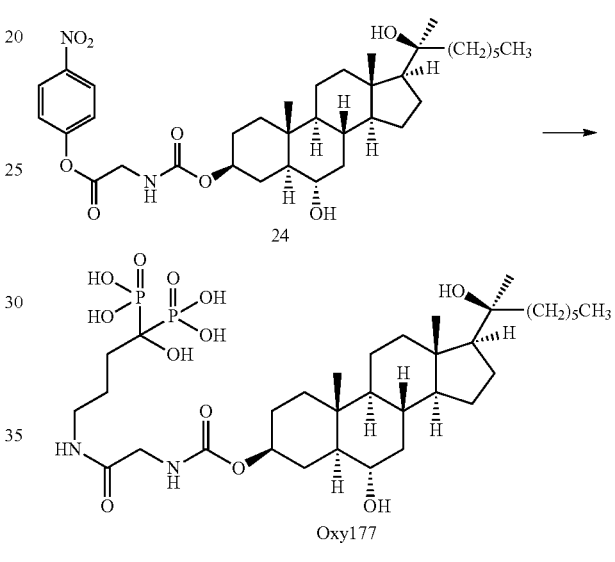

Oxy177 was prepared from 24 following the procedure described for the synthesis of Oxy175. ¹H-NMR key resonances (500 MHz, D₂O): δ 4.43 (bs, 1H), 3.80 (m, 1H), 3.67 (m, 1H), 3.37 (bs, 1H), 3.12 (bs, 2H), 2.11-0.40 (broad) ppm. HRMS: calc for C₃₄H₆₁NO₁₂P₂ [M-H]⁻: 751.3705; found: 751.3665 m/z.

EXAMPLE 7

Synthesis of Oxy178

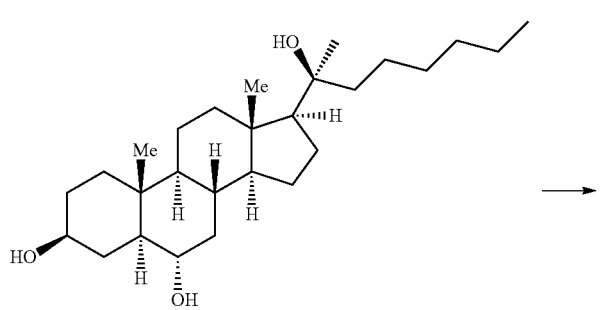

OXY133

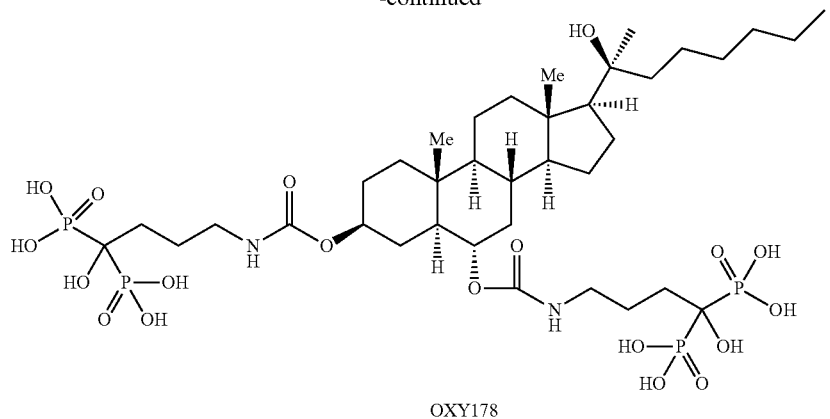

OXY178

OXY178 has direct carbamate linkages between OXY133 and alendronic acid at the 3 and 6-positions of OXY133. OXY178 can be synthesized directly from OXY133 and require no protecting group manipulation.

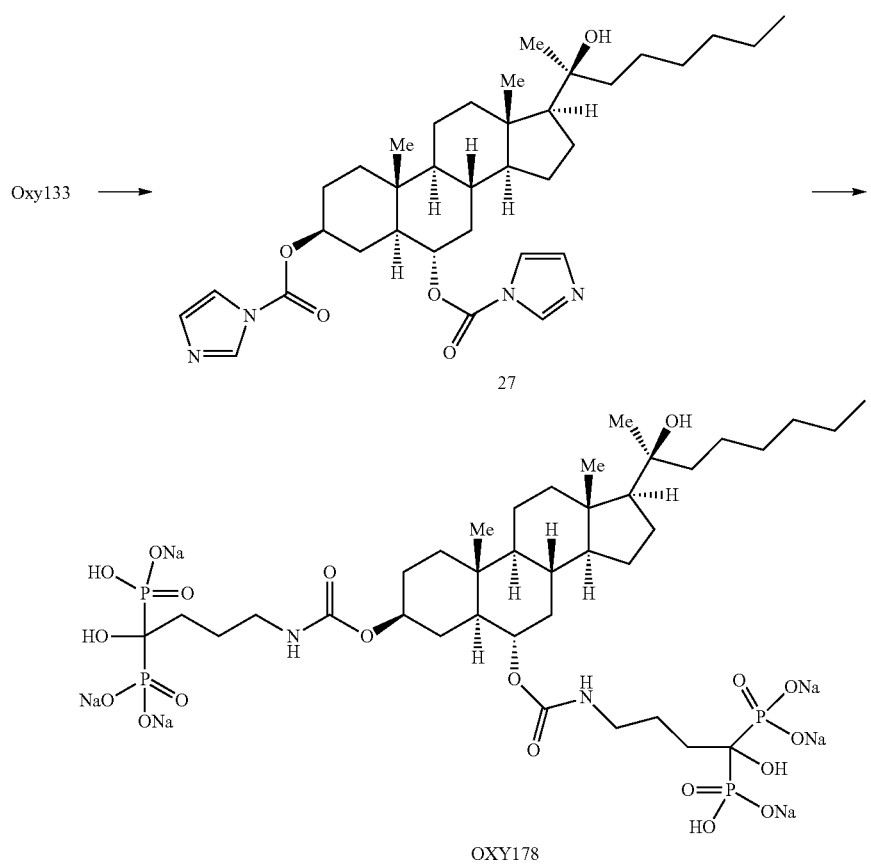

To a solution of Oxy133 (520 mg, $1.2 \times 10^{-3}$ mol, 1 eq) in anhydrous THF (6 mL) was added carbonyldiimidazole (1.4 g, $8.4 \times 10^{-3}$ mol, 7 eq) in one portion. After 16 h at room temperature, the mixture was diluted with water (20 mL) and EtOAc (20 mL). After separation of the organic layer, the aqueous layer was back-extracted with EtOAc (2×20 mL). The combined organic layers were washed with brine and dried over $Na_2SO_4$. The crude 27 (which contains residual imidazole) was used without further purification. $^1$H-NMR (CDCl$_3$, 300 MHZ) δ: 8.12, 8.01 (2H, s), 7.4, 7.38 (2H, s), 7.06, 7.04, (2H, s), 4.81 (2 H, m), 2.19 (1H, m), 2.10-1.90 (3 H, m), 1.85-1.60 (7 H, m), 1.55-1.38 (7H, m), 1.25 (11H, brs), 1.20-0.95 (4 H, m), 0.90 (3H, m), 0.86 (3H, s), 0.80 (3H, s) 0.62 (2H, m) ppm.

Oxy178 was synthesized from crude 27 (0.24 g, ca. 0.4 mmol) according to the procedure for the synthesis of Oxy166 to afford after lyophilization 65 mg (15%) of Oxy178. $^1$H-NMR key resonances (D$_2$O, 300 MHz) δ: 4.41 (2 H, m), 3.00 (4H, m), 2.10-0.62 (broad). HRMS: calc for C$_{37}$H$_{69}$N$_2$O$_{12}$P$_2$ [M-H]$^-$: 969.3450; found: 969.3100 m/z.

Mono-carbamate analogs of Oxy178, shown below, can be made.

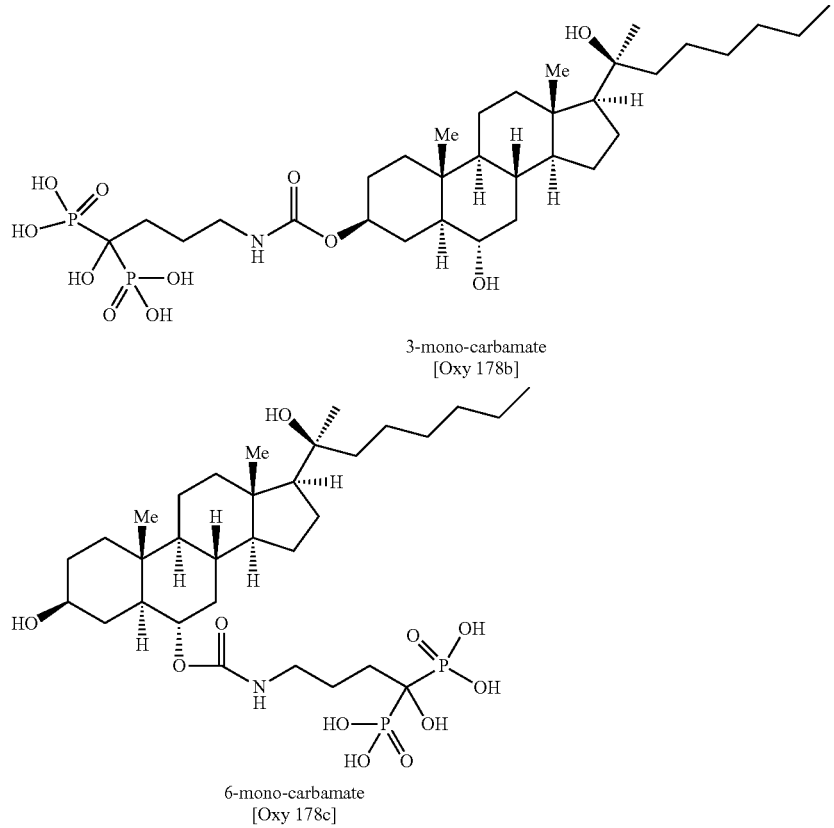

3-mono-carbamate
[Oxy 178b]

6-mono-carbamate
[Oxy 178c]

The present invention is not limited to the examples provided in this specification. For example, in an embodiment, OXY133-ALN conjugates may be conjugated at the 20-position of OXY133. One of ordinary skill in the art will appreciate that OXY133-ALN conjugates may comprise different linker units.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject.

In certain representations of chemical structures, the fully protonated form of a compound is shown. Unless otherwise specifically indicated, it is to be understood that this compound could also be a salt form of the compound. In certain representations of chemical structures, the salt form of a compound is shown. Unless otherwise specifically indicated, it is to be understood that this compound could also be that salt form with a different degree of protonation, could also be a different salt form, or could be the fully protonated form of the compound.

In another embodiment, these oxysterols and oxysterol-bisphosphonate conjugates can be a part of a pharmaceutical composition that can be used as a therapeutic agent for the treatment of osteoporosis.

EXAMPLE 8

Biological Activity of OXY133-ALN Conjugates

Oxy133-ALN conjugates were tested in M2-10B4 osteo-progenitor cells to ascertain osteogenic activity and confirm their mechanism of action in inducing osteogenic differentiation. Alkaline phosphatase (ALP) activity, induction of the expression of osteogenic differentiation marker genes (ALP; bone sialoprotein (BSP); and osterix (OSX)), and $^{45}$Ca incorporation as a measure of extracellular matrix mineralization were assayed by our previously reported protocols. The inventors have shown that these in vitro assays translate into in vivo stimulation of bone formation in a variety of animal models. The gene expression for ALP, BSP and OSX induced by the OXY133-ALN conjugates were measured after 6 and 14 days of treatment, the results after 6 days are shown in FIG. 1.

Figure 2:
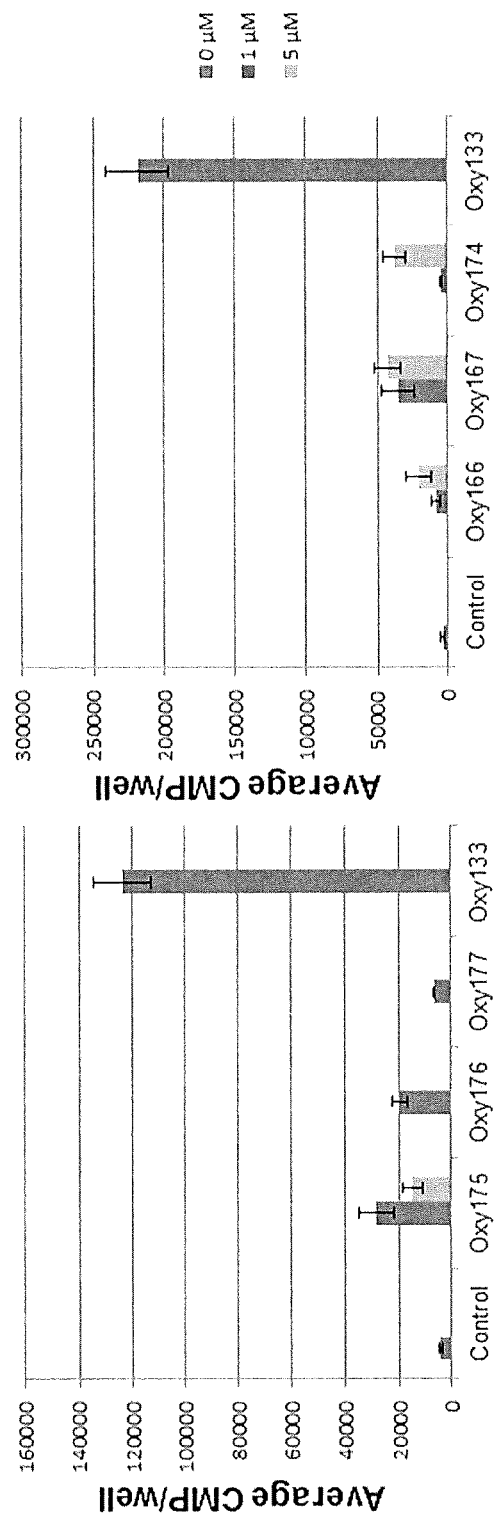
FIG. 2 shows the effect of OXY133-ALN conjugates on mineralization observed in M2 cells after 30 days.

The succinate-linked series (Oxy166, Oxy167, Oxy174) and the carbamate series (Oxy175, Oxy176, and Oxy177) were assayed as groups. The OXY133-ALN conjugates generally induced osteogenic gene expression when compared to control untreated cells and to a lesser degree than unconjugated OXY133. It may be that OXY133 must be released from the OXY133-ALN conjugates in order to induce osteogenic gene expression. The OXY133-ALN compounds showed varying levels of activity in these in vitro experiments according to the expected susceptibility of the linker to cleavage by esterases, indicating 'tune-ability' based on the position and the identity of the linker. In both series, the mono C-6 functionalized compound was the most active (Oxy167, Oxy175) and, consistent with the relative stability to enzymatic hydrolysis, the succinate-linked series (Oxy167) was more active than the carbamate-linked series (Oxy175). This result was mirrored in ALP activity induction experiments. Pre-treatment of cells with 4 µM of the specific Hh pathway inhibitor cyclopamine inhibited the induction of osteogenic genes by all oxysterols, indicating the role of Hh pathway in mediating their osteogenic effects, and similar to what has been observed for unconjugated OXY133 and other osteogenic oxysterols. A quantitative $^{45}Ca$ mineralization assay was performed with analogues and unconjugated OXY133 over a 30-day incubation period in M2 cells as shown in FIG. 2. Thus, all compounds caused significant levels of mineralization, suggesting that long-term functionality of cells induced by the oxysterols to undergo osteogenic differentiation may be positively affected. The results demonstrate varying degrees of activity depending on the structure of the Oxy133-ALN conjugate, and all compounds were associated with significant amounts of mineralization.

EXAMPLE 9

Examination of the Hydroxyapatite (HAP) Binding Capacity of OXY133-ALN Conjugates The bone binding properties of bisphosphonates are due to their affinity for calcium in hydroxyapatite (HAP). Relative HAP binding capacity can be measured by incubating a solution of an analyte with HAP and measuring the proportion of compound remaining in the supernatant. This HAP binding assay is effective with bisphosphonates known to exhibit avid bone attachment clinically and translates to bone deposition in vivo for a variety of other compounds. As shown in FIG. 3, an in vitro HAP binding assay was conducted that was analogous to these studies but adapted to the unique nature of the Oxy133-ALN conjugates. Because ALN and the Oxy133-ALN conjugates are UV/Vis inactive, manifest broad $^1H$-NMR resonances, and are difficult to detect with mass spectroscopy, a $^{31}P$-NMR based method was employed to measure the fraction of analyte unbound to the HAP. This approach is advantageous because samples can be directly analyzed without derivatization or undue manipulation and can be reliably integrated against an external standard unexposed to the assay conditions. Reliable quantification of a range of analytes can be obtained by using an inverse-gated decoupling pulse sequence and sufficiently long relaxation delays ($d_1$).

Figures 3A, 3B:
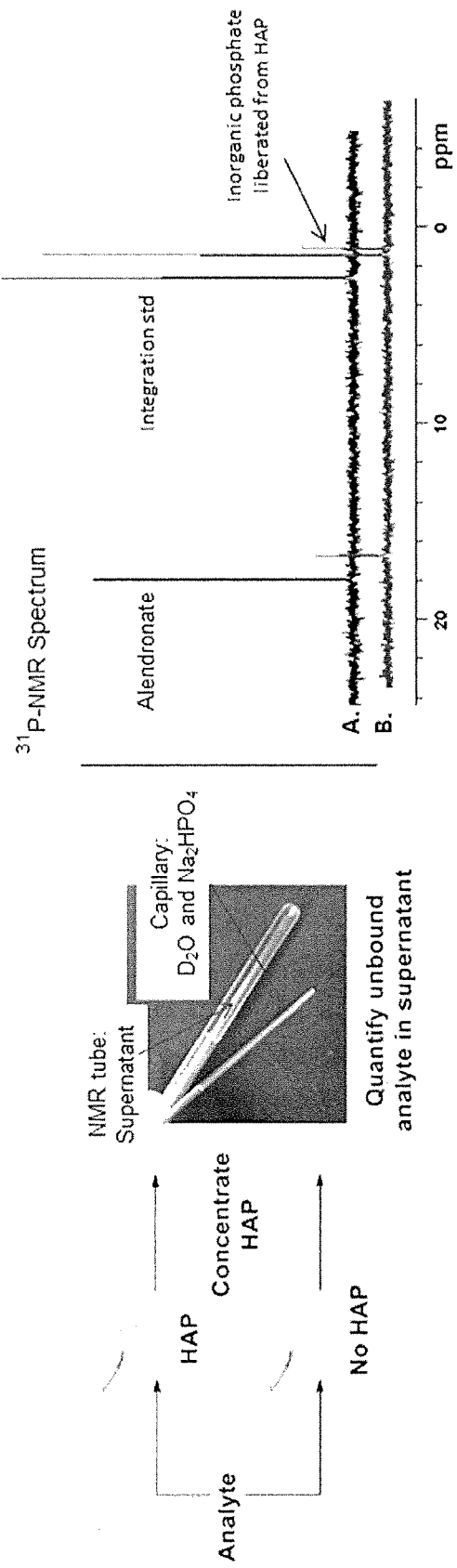
FIG. 3A illustrates the $^{31}$P-NMR visualized HAP binding assay procedure and experimental design.
FIG. 3B shows results from the HAP binding assay.

The HAP binding assay was carried out under the following conditions: 1 mL of 4 mM analyte in 50 mM tris buffer at pH 7.5 is incubated with HAP (or no HAP for control) by inversion for 15 minutes. HAP is pelleted by mild centrifugation and the supernatant is directly added to an NMR tube containing an integration standard and $D_2O$. $^{31}P$-NMR was acquired at 122 MHz using an inverse-gated decoupled pulse sequence with a 30 degree pulse angle and a relaxation delay of 30 s (doubling relaxation time did not affect relative integration areas). The procedure is illustrated in FIG. 3A. As shown in FIG. 3B, $^{31}P$-NMR spectra show the control (A) and HAP treated sample of alendronate (B), which is integrated against an internal standard and remains constant.

The binding strengths of the OXY133-ALN conjugates of the present invention relative to ALN were determined and any differences in binding affinity contributed by the degree (mono- vs. bis-ALN linked conjugates), position (C3-OH vs. C6-OH), and nature (succinate vs. glycinate) of the Oxy133-ALN conjugates noted. ALN was used as a positive control and benzyl phosphonic acid (BnP) as an established negative control. 600 mg of HAP was used for the "large HAP loading" condition (FIG. 4A) and 150 mg of HAP was used for the "low HAP loading" condition (FIG. 4B).

Experimental conditions: 1 mL of 4 mM analyte in 50 mM tris buffer pH 7.5 is incubated with specified amount of HAP (or no HAP for control) by inversion for 15 min. HAP is pelleted by mild centrifugation and the supernatant is directly added to an NMR tube containing integration std and $D_2O$. $^{31}P$-NMR acquired at 122 MHz using inverse-gated decoupled pulse sequence with a 30 degree pulse angle, a relaxation delay of 30s (doubling relaxation time did not affect relative integration areas). $^{31}P$-NMR spectra (FIG. 3B) show control (A—blue spectra) and HAP treated sample of alendronate (B—red spectra) which is integrated against an internal standard which remains constant.

Figures 4A, 4B, 4C:
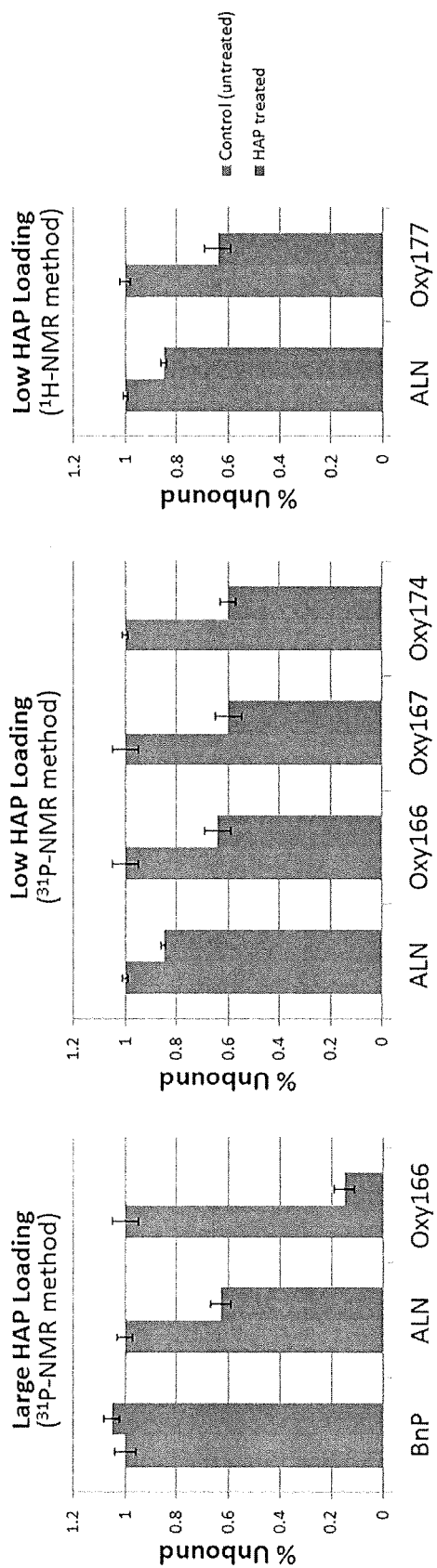
FIG. 4A shows results of the HAP binding assay according to the conditions described for the experiment of FIG. 3A with 600 mg of HAP for the "large HAP loading" condition.
FIGS. 4B and 4C show results of the HAP binding assay according to the conditions described for the experiment of FIG. 3A with 150 mg of HAP for the "low HAP loading" condition.

Oxy166 was assayed relative to the controls and exhibited more potent HAP binding relative to ALN (FIG. 4A). Because the unbound Oxy166 approached the level of detection, the various Oxy133-ALN conjugates were examined with a lower HAP loading (FIG. 4B). Because $^{31}P$-signal broadening resulted from the possible tautomeric forms of the carbamate series, a $^1H$-NMR method was developed. Performing the HAP binding assay in $D_2O$ with an internal integration standard (maleic acid) gave identical values for ALN obtained with the $^{31}P$ method and revealed that Oxy177 possessed a binding affinity equivalent to the rest of the OXY-ALN series (FIG. 4C). All of the Oxy133-ALN conjugates possessed more HAP binding capacity than ALN alone. Increasing lipophilicity adjacent to the bone-seeking moiety appears to improve HAP binding in vitro. The nature and degree of ALN conjugation does not appear to affect HAP binding. Short linkers were employed in the Oxy133-ALN conjugates, so that this is consistent with a model in which binding to the HAP surface occurs at limited 'active kink sites'. That relatively minor changes in structure, such as the regiochemistry of attachment or the type of linker, did not affect the observed binding was consistent with the highly potent HAP binding of ALN. Thus, from measurements of the HAP binding affinity of Oxy133-ALN conjugates, strong HAP binding that was independent of the degree, site, or nature of the alendronate attachment was observed. This may correlate with in vivo deposition of Oxy133-ALN conjugates in bone. Based on their HAP binding affinity, which was similar among the Oxy133-ALN conjugates, the Oxy133-ALN conjugates should exhibit strong bone affinity and are promising for therapy.

Pharmaceutical Compositions and Administration

The compounds of embodiments of the present invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fme inert powdered carrier and inhaled by the subject or insufflated. Such compositions and preparations should contain at least 0.1% of a compound of an embodiment of the present invention. The percentage of the compositions and preparations may, of course, be varied and may conveniently be between about 2% to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, time release pills, and time release polymers or nanoparticles.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form.

The compounds can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

All documents, references, and information, including, but not limited to, journal articles, patent applications, and patents, that are mentioned, cited, or referred to in this application are hereby incorporated by reference in their entirety as if each had been individually incorporated. Such documents include, but are not limited to, U.S. Patent Application Publication numbers 2006-0270645A1, 2006-0251735A1, 2009-0202660A1, 2009-0220562A1, 2010-0034781A1, 2010-0048944A1, 2010-0105645A1, 2010-0012030A1, 2011-0008297A1, and 2012-0309730A1 and International Application Publication numbers WO2014/179756, WO2013/169399, WO2013/169397, and WO2011/006087.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. The compound of the formula

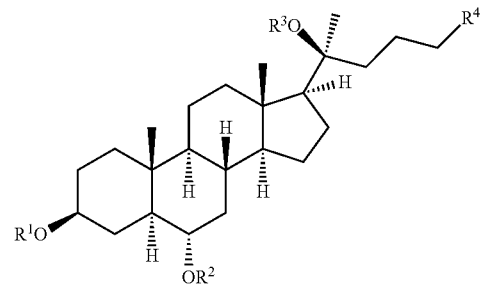

wherein $R^1$, $R^2$, and $R^3$ are independently selected from the group consisting of hydrogen,

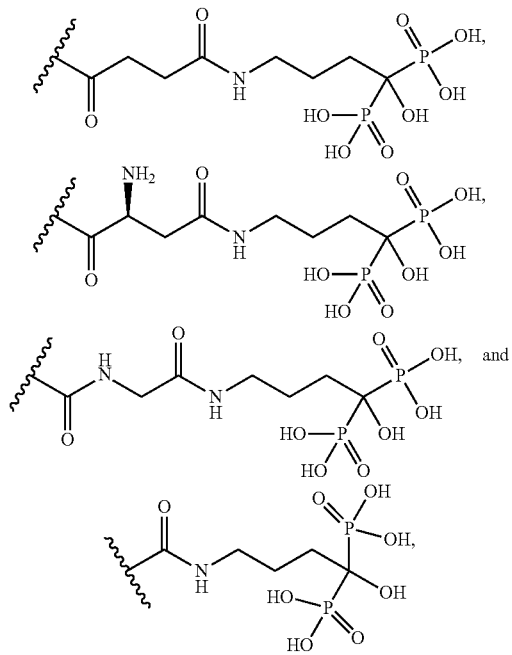

wherein at least one of $R^1$, $R^2$, and $R^3$ is not hydrogen, and wherein $R^4$ is alkyl from 1 to 5 carbons; or
a pharmaceutically acceptable salt thereof.
2. The compound of claim 1, of the formula

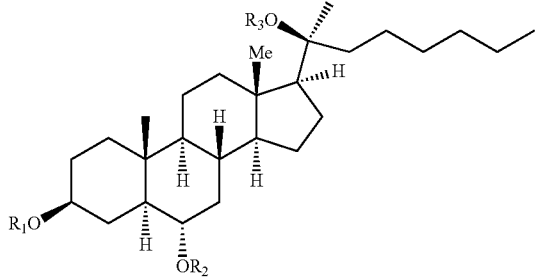

wherein $R^1$, $R^2$, and $R^3$ are independently selected from the group consisting of hydrogen,

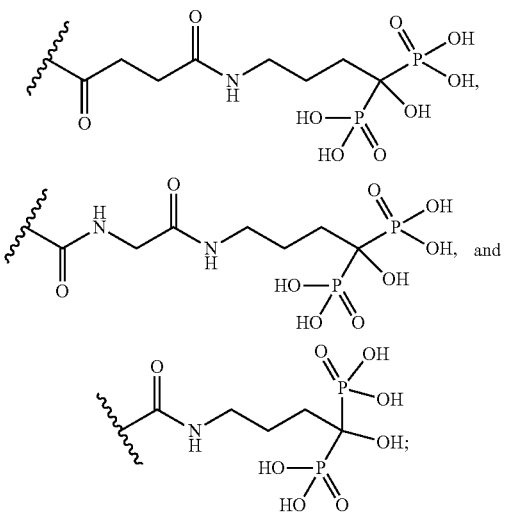

a pharmaceutically acceptable salt thereof.
3. The compound of claim 2, of the formula

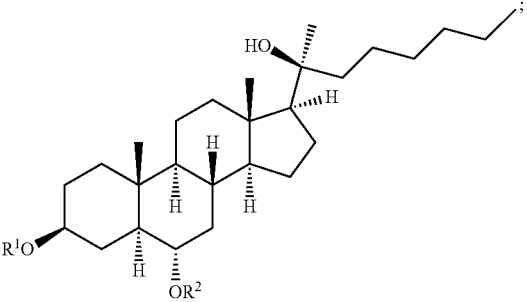

or
a pharmaceutically acceptable salt thereof.
4. The compound of claim 3, of the formula

[Oxy166]

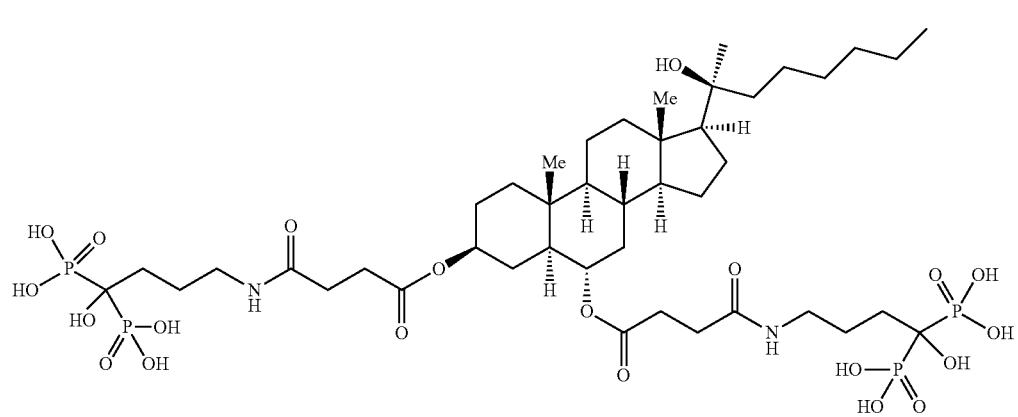

or a pharmaceutically acceptable salt thereof.

5. The compound of claim 4, wherein the compound is a sodium salt.

6. The compound of claim 3, of the formula

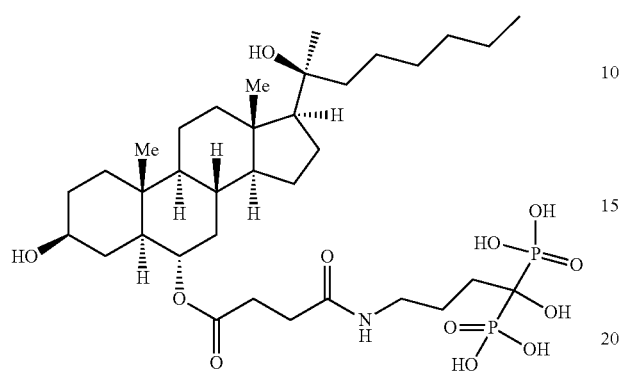

[Oxy167]

or a pharmaceutically acceptable salt thereof.

7. The compound of claim 6, wherein the compound is a sodium salt.

8. The compound of claim 3, of the formula

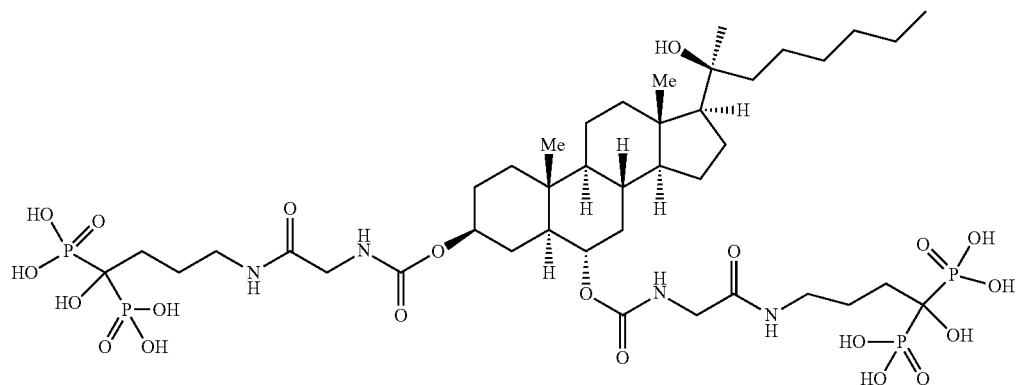

[Oxy176]

or a pharmaceutically acceptable salt thereof.

9. The compound of claim 8, wherein the compound is a sodium salt.

10. The compound of claim 3, of the formula

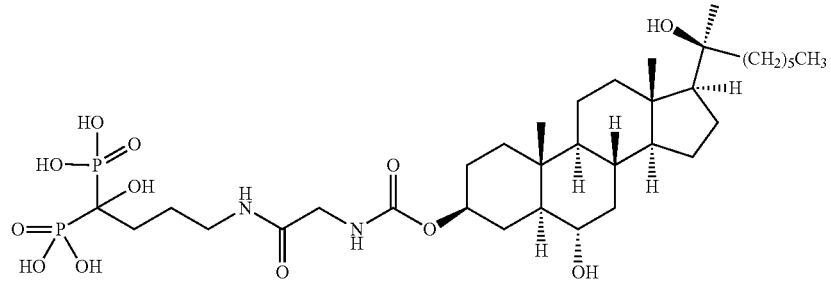

[Oxy177]

or a pharmaceutically acceptable salt thereof.

11. The compound of claim 10, wherein the compound is a sodium salt.

12. The compound of claim 3, of the formula

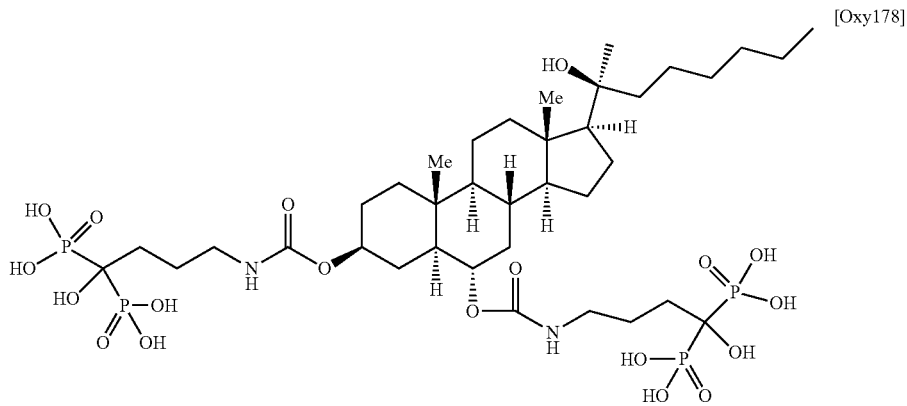

[Oxy178]

or a pharmaceutically acceptable salt thereof.

13. The compound of claim 12, wherein the compound is a sodium salt.

14. The compound of claim 3, of the formula

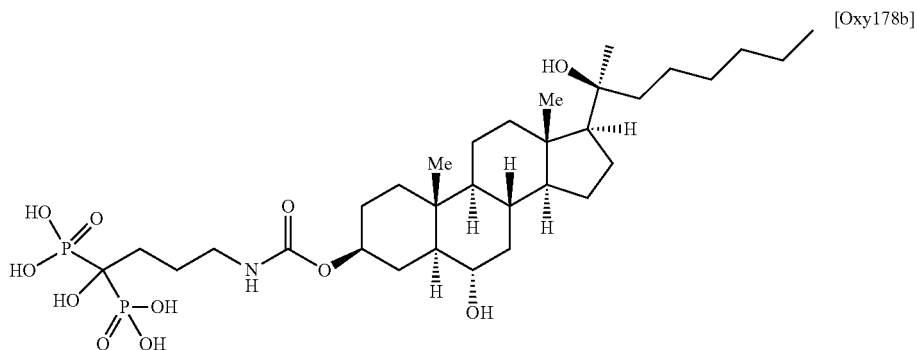

[Oxy178b]

or a pharmaceutically acceptable salt thereof.

15. The compound of claim 14, wherein the compound is a sodium salt.

16. The compound of claim 3, of the formula

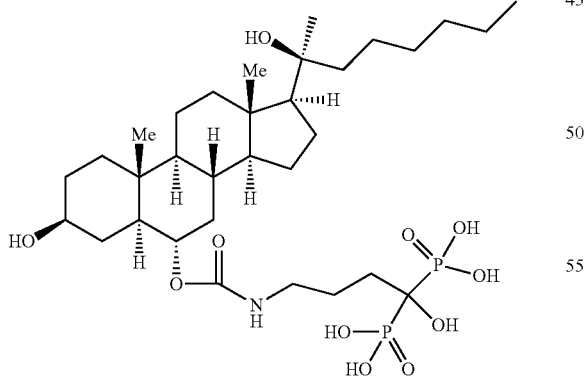

[Oxy178c]

or a pharmaceutically acceptable salt thereof.

17. The compound of claim 16, wherein the compound is a sodium salt.

18. A pharmaceutical composition comprising a compound of claim 1 and a pharmaceutically acceptable carrier or diluent.

* * * * *